United States Patent
Faithfull et al.

[11] Patent Number: 6,041,777
[45] Date of Patent: Mar. 28, 2000

[54] METHODS AND APPARATUS FOR CLOSED-CIRCUIT VENTILATION THERAPY

[75] Inventors: Nicholas Simon Faithfull, La Jolla; Ernest G. Schutt, San Diego, both of Calif.

[73] Assignee: Alliance Pharmaceutical Corp., San Diego, Calif.

[21] Appl. No.: 08/566,023

[22] Filed: Dec. 1, 1995

[51] Int. Cl.[7] .................................................. A61M 15/00
[52] U.S. Cl. ............................ 128/200.24; 128/203.12; 128/204.18; 128/913
[58] Field of Search ................. 128/200.24, 203.12, 128/204.18, 913; 604/20

[56] References Cited

U.S. PATENT DOCUMENTS

| | | | |
|---|---|---|---|
| 3,991,790 | 11/1976 | Russell | 137/819 |
| 4,232,665 | 11/1980 | Vaseen | 128/200.24 |
| 4,573,462 | 3/1986 | Baum. | |
| 4,928,683 | 5/1990 | Westerkamp et al. | |
| 5,119,810 | 6/1992 | Kiske et al. | |
| 5,158,536 | 10/1992 | Sekins et al. | 604/20 |
| 5,322,057 | 6/1994 | Raabe et al. | 128/203.12 |
| 5,335,650 | 8/1994 | Shaffer et al. | 128/913 |
| 5,437,272 | 8/1995 | Fuhrman. | |
| 5,492,109 | 2/1996 | Hirschl et al. | 128/913 |
| 5,540,225 | 7/1996 | Schutt | 128/913 |
| 5,590,651 | 1/1997 | Shaffer et al. | 128/913 |

FOREIGN PATENT DOCUMENTS

| | | |
|---|---|---|
| 0678305A1 | 10/1995 | European Pat. Off. . |
| 2000353 | 9/1993 | Germany . |
| 2054387 | 2/1981 | United Kingdom . |
| WO 9103267 | 3/1991 | WIPO . |
| 9219232 | 11/1992 | WIPO . |

OTHER PUBLICATIONS

Schepp, et al. "Automatic Ventilation During Closed-Circuit Anaesthesia" *Anaesthesia–Innovations in Management* eds. Erdmann, et al. Springer-Verlag pp. 48–53 (1985).

Brochure of MRM–6000 Metabolic Analyzer from Waters Instruments, Inc., Rochester, MN 55903–6117 in 7 pages.

*Primary Examiner*—V. Millir
*Assistant Examiner*—William J. Deane, Jr.
*Attorney, Agent, or Firm*—Knobbe, Martens, Olson & Bear, LLP

[57] ABSTRACT

Methods and apparatus are provided which allow for closed-circuit ventilation for the treatment or diagnosis of disorders. The closed-circuit ventilation apparatus of the present invention provide a closed-circuit respirator that isolates the gas flow path from the ventilator apparatus. This allows the prolonged administration of expensive materials such as fluorochemicals without excessive loss due to evaporation. As such the provided methods an apparatus are particularly applicable to liquid ventilation including partial liquid ventilation and total liquid ventilation.

81 Claims, 6 Drawing Sheets

VENTILATION SYSTEM

METHODS AND APPARATUS FOR CLOSED-CIRCUIT VENTILATION THERAPY

FIELD OF THE INVENTION

The present invention relates to methods and apparatus for respiratory ventilation and, more particularly, relates to closed-circuit ventilation the treatment or diagnosis of various disorders.

BACKGROUND OF THE INVENTION

Respiration involves the introduction of fresh gases, especially oxygen, to the lung during inspiration and the removal of waste gases, particularly carbon dioxide, during expiration. In healthy individuals respiration is normally effected by spontaneous ventilation or breathing which results in the introduction of the necessary gases. Unfortunately, a number of physiological and pathological processes may compromise normal pulmonary function leading to the inhibition of effective respiration or total respiratory failure. In such cases respiratory therapy, often involving artificial ventilation to some degree, is indicated. For example, respiratory therapy is often indicated for patients undergoing surgery or those suffering disorders and diseases of the pulmonary air passages. In particular, patients suffering from lung contusion, diver's lung, post-traumatic respiratory distress, post-surgical atelectasis, irritant injuries, septic shock, multiple organ failure, Mendelssohn's disease, obstructive lung disease, pneumonia, pulmonary edema or any other condition resulting in lung surfactant deficiency or respiratory distress are strong candidates for respiratory therapy. Typically, such respiratory therapy involves the use of mechanical ventilators.

Mechanical ventilators are simply clinical devices that effect ventilation or, in other words, cause airflow into the lungs. More specifically, such devices typically force air into the lungs during the inspiration phase of the breathing cycle but allow a return to ambient pressure during spontaneous exhalation. The forced influx of fresh air by mechanical ventilation facilitates the pulmonary mediated processes that comprise respiration in mammals. One of these processes, removal of waste gases, is a primary mechanism by which carbon dioxide is excreted from the body. In normal gas mediated carbon dioxide removal, fresh air is brought into contact with the alveoli (alveolar ventilation) thereby promoting gas exchange wherein carbon dioxide passes from the body and is exhaled. The other essential bioprocess, oxygenation, comprises the absorption of oxygen into the blood from the lungs. It is primarily a function of the mechanism whereby the partial pressure of oxygen ($PO_2$) in pulmonary capillary blood equilibrates with the partial pressure of oxygen in inflated alveoli. The oxygen gradient between alveolus and capillary favors transfer of oxygen into blood because the repeated influx of fresh oxygen through ventilation (spontaneous or assisted) maintains alveolar $PO_2$ at higher levels than capillary $PO_2$. Modern mechanical ventilators are designed to provide ventilation by regulating tidal volume (breath), flow rate, delivery profile and respiratory flow thereby controlling carbon dioxide excretion. Because they can also regulate airway pressure and the concentration of inspired oxygen they offer control over oxygenation as well.

At least twenty makes and models of mechanical ventilators are used in North America today. Almost all the ventilators used in operating rooms, recovery rooms and intensive care units are volume-controlled ventilators. With a device of this type the operator may set tidal volume, respiratory rate, and inspiratory rate allowing the ventilator to deliver a set volume of gas regardless of the airway pressure. Such devices usually have a pressure cutoff to prevent damage to the lungs. In contrast, pressure-controlled ventilators are standard in neonatal intensive care, in chronic ventilator management and during patient transport. Pressure-controlled ventilators typically allow the operator to select the respiratory rate, the inspiratory gas flow and the peak airway pressure. The ventilator then delivers inspired gas, while monitoring the tidal volume, until the desired pressure is reached. Each of these types of mechanical ventilators incorporate a number of sophisticated features which allow unparalleled control over the delivery of gases to the lung. For example, typical mechanical ventilators offer a number of complex delivery profiles designed to optimize the introduction of gases into the lung taking into account the physical state of the patient, therapeutic requirements and the respiration pattern of the patient under different conditions. In order to meet the diverse of patients requiring ventilation therapy, common mechanical ventilators offer several ventilation modes, each having a variety of programmable parameters, offering an almost unlimited versatility. Some common ventilation modes include controlled mechanical ventilation, assist control, intermittent mandatory ventilation, synchronized intermittent mandatory ventilation, continuous positive airway pressure, pressure controlled ventilation, pressure controlled inverse ratio ventilation, pressure support as well as combinations of modes. Unfortunately, in both types of commercially available ventilators the expired gases, including any bioactive agents introduced during inspiration or exhaled pathogenic material, are typically released into the environment during use.

In contrast to standard mechanical ventilation, liquid ventilation is a technique which involves introducing an oxygenated liquid medium into the pulmonary air passages for the purposes of waste gas exchange and oxygenation. Essentially, there are two separate techniques for performing liquid ventilation, total liquid ventilation and partial liquid ventilation. Total liquid ventilation or "TLV" is the pulmonary introduction of warmed, extracorporeally oxygenated liquid respiratory promoter (typically fluorochemicals) at a volume greater than the functional residual capacity of the subject. The subject is then connected to a liquid breathing system and tidal liquid volumes are delivered at a frequency depending on respiratory requirements while exhaled liquid is purged of $CO_2$ and oxygenated extracorporeally between the breaths. Conversely, partial liquid ventilation or "PLV" involves the use of conventional mechanical ventilation in combination with pulmonary administration of a respiratory promoter capable of oxygenation. As with TLV the respiratory promoter typically comprises fluorochemicals which may be oxygenated extracorporeally prior to introduction. In the instant application the term "liquid ventilation" will be used in a generic sense and shall be defined as the introduction of any amount of respiratory promoter into the lung, including the techniques of both partial liquid ventilation and total liquid ventilation.

The concept of liquid ventilation originated more than thirty years ago when it was shown that animals submerged in a hyperoxygenated respiratory promoter (saline) could breath the liquid and successfully resume gas breathing. For practical purposes liquid ventilation became a viable technique when it was discovered that fluorochemicals could be used as the respiratory promoter. Liquid breathing using oxygenated fluorochemicals has been demonstrated on several occasions. For example, an animal submerged in an oxygenated fluorochemical liquid may exchange oxygen and carbon dioxide normally when the lungs fill with the fluorochemical. Although the work of breathing is increased in total submersion experiments, the animal can derive adequate oxygen for survival by breathing the oxygenated fluorochemical liquid. In particular, it has been established that total liquid ventilation may keep mammals alive for extended periods prior to returning them to conventional gas breathing.

Use of liquid ventilation may provide significant medical benefits which are not available through the use of conventional mechanical ventilators employing a breathable gas. For example, the weight of the respiratory promoter opens alveoli with much lower ventilator pressure than is possible with gas. Additionally, liquid ventilation using fluorochemicals as the respiratory promoter has been shown to be effective in rinsing out congestive materials associated with respiratory distress syndrome. Moreover, liquid ventilation has been shown to be a promising therapy for the treatment of respiratory distress syndromes involving surfactant deficiency or dysfunction. Elevated alveolar surface tension plays a central role in the pathophysiology of the Respiratory Distress Syndrome (RDS) in premature infants and is thought to contribute to the dysfunction in children and adults. Liquid ventilation, particularly using fluorochemicals, is effective in surfactant-deficient disorders because it eliminates the air/fluid interfaces in the lung and thereby greatly reduces pulmonary surface tension. Moreover, liquid ventilation can be accomplished without undue alveolar pressures or impairing cardiac output and provides excellent gas exchange even in premature infants. Other beneficial aspects associated with liquid ventilation include facilitation of pulmonary drug delivery and lung cancer hyperthermia.

Despite the undeniable advantages associated with liquid ventilation, the use of total liquid ventilation as a therapy presents significant complications. TLV requires that tidal breaths of the respiratory promoter be mechanically cycled into and out of the lungs. Unmodified conventional mechanical ventilators, such as those discussed above, will not work in total liquid ventilation procedures. Total liquid breathing in a hospital setting requires dedicated ventilation equipment, currently not available commercially, capable of handling liquids. Moreover, the respiratory promoter must be oxygenated and purged of carbon dioxide extracorporeally, a difficult process requiring specialized equipment and large volumes of oxygen. Further, extracorporeal scrubbing of the respiratory promoter, particularly fluorochemicals, currently results in substantial losses as part of the medium is vaporized during the procedure. In addition, as the respiratory promoter is oxygenated and purged of carbon dioxide outside the body while being cyclically delivered to the lungs, a large and potentially expensive priming volume of respiratory promoter is required to fill the liquid breathing device. Accordingly, capital costs associated with liquid breathing are considerable.

In order to obviate many of these complications, yet still retain the benefits inherent in liquid ventilation, the technique of partial liquid ventilation was developed. Partial liquid ventilation, as described in Fuhrman, U.S. Pat. No. 5,437,272 and published PCT Application No. WO 92/19232, is a safe and convenient clinical application of liquid breathing using oxygenated fluorochemicals. In PLV a liquid, vaporous or gaseous respiratory promoter (again typically a fluorochemical) is introduced into the pulmonary air passages at volumes ranging from just enough to interact with a portion of the pulmonary surface all the way up to the functional residual capacity of the subject. Respiratory promoters are any compound that functions, systemically or pulmonarily, to improve gas exchange and respiration efficiency. Respiratory gas exchange is thereafter maintained for the duration of the procedure by continuous positive pressure ventilation using a conventional open-circuit gas ventilator. Like total liquid ventilation, the pulmonary introduction of the respiratory promoter eliminates surface tension due to pulmonary air/fluid interfaces as well as improving pulmonary function and gas exchange in surfactant deficiency and other disorders of the lung. As PLV does not require extracorporeal oxygenation and scrubbing or the cyclic introduction of the respiratory promoter to the lung, the use of specialized expensive equipment is not required. Rather, well established conventional off-the-shelf ventilators may be used to provide the necessary oxygenation and carbon dioxide purging in vivo. Moreover, as it is predominantly gas rather than liquid that moves in tidal fashion with each breath, the airway pressures required for the procedure may be much lower than during TLV. Thus, the potential for barotrauma is substantially reduced. Finally, when the procedure is over the introduced the liquid, gaseous or vaporous respiratory promoter is simply allowed to evaporate rather than being physically removed as in TLV.

As previously indicated, fluorochemicals are the preferred respiratory promoter for both TLV and PLV. In general, fluorochemicals compatible with liquid ventilation will be clear, odorless, nonflammable, and essentially insoluble in water. Additionally, preferred fluorochemicals are denser than water and soft tissue, have a low surface tension and, for the most part, a low viscosity. In particular, brominated fluorochemicals are known to be safe, biocompatible substances when appropriately used in medical applications. It is additionally known that oxygen, and gases in general, are highly soluble in some fluorochemicals. For example, some fluorochemical liquids may dissolve over twenty times a much oxygen and over thirty times as much carbon dioxide as a comparable amount of water. Oxygenatable fluorochemicals act as a solvent for oxygen. They dissolve oxygen at higher tensions and release this oxygen as the partial pressure decreases. Carbon dioxide behaves in a similar manner. In addition to carrying gases and removing waste products, respiratory promoters such as fluorochemicals may be used as pulmonary drug delivery vehicles, either in conjunction with liquid ventilation or as independent therapy. For example, aerosol delivery systems may rely on a mixture of a therapeutically active agent with one or more respiratory promoters to increase dispersion, efficacy and stability of the bioactive agent. Moreover, selected respiratory promoters, including, in particular, fluorochemicals, have been shown to have pulmonary and systemic anti-inflammatory effects. Accordingly, despite relatively high costs, it is desirable to employ fluorochemicals as the respiratory promoter of choice in current liquid ventilation procedures and pulmonary drug delivery.

While liquid ventilation is a significant improvement over conventional ventilation, the escape of the respiratory promoter, particularly fluorochemicals, into the environment in the form of vapors, compromises the effectiveness of both TLV and PLV therapy. During normal fluorochemical ventilation procedures the generation and release of such vapor may be significant. For example, in current PLV therapy conventional mechanical ventilators release the expired gas, including fluorochemical vapors, into the environment or store them for future disposal. In adult PLV treatments evaporative fluorochemical losses may correspond to approximately 10–20% of functional residual capacity per hour or approximately 400 to 800 grams of fluorochemical per hour. Significant fluorochemical losses also occur during TLV treatments. In this case, the greatest losses occur as the circulated liquid medium is subject to extracorporeal oxygenation and carbon dioxide purging. In particular, a great deal of gaseous oxygen must be introduced into the respiratory promoter to disassociate and purge the accumulated carbon dioxide prior to reintroduction of the respiratory promoter into the body. The majority of the oxygen passes through the respiratory promoter and is vented, carrying with it carbon dioxide and, unfortunately, fluorochemical vapor. Of course, if the therapy is to be continued additional respiratory promoter must be added to maintain effective residual volumes. As fluorochemical liquids and other respiratory promoters suitable for liquid ventilation can be relatively expensive, such losses can substantially raise the cost of such therapies. Moreover, in either type of treatment, the loss of respiratory promoter complicates both dosing regimens and monitoring the current volume of material in the lung.

Besides the loss of expensive material, the use of fluorochemical based respiratory promoters can damage conventional ventilation equipment which incorporate materials that are not compatible. For example, a number of engineering plastics used in current ventilators tend to swell in the presence of fluorochemicals. In other currently used materials, exposure to fluorochemicals will leach plasticizers causing the material to become brittle and subject to failure under much less stress. Further, modern conventional ventilators contain a number of delicate sensors for monitoring the levels and condition of both the inspiratory and respiratory gases. As with the ventilators themselves, many of these sensors incorporate materials that are not fully compatible with fluorochemicals or other potential respiratory promoters. Accordingly, the use of fluorochemicals with conventional systems may lead to a degradation of sensory data and inaccurate readings if the apparatus is not properly monitored and maintained. Such materials problems can be severe, if not fatal, handicaps when trying to gain regulatory approval of a therapeutic method or incorporation of a specific device into a preapproved treatment. Materials problems aside, each different ventilator used for liquid ventilation, including commercially available machines, will likely have to be individually cleared by the Food and Drug Administration prior to use in such treatments. Obtaining such clearance, if possible, can be an expensive and time consuming process that can limit the widespread use of an otherwise proven and effective therapy.

Unfortunately, no effective means of addressing these problems or providing closed-circuit ventilation therapy currently exists. For instance, as indicated above commercially available mechanical ventilators vent, as a matter of course, any beneficial gases or vapors present in the pulmonary air passages along with the waste gases. On the other hand, pulmonary administration devices employing sealed delivery systems lack the necessary versatility and sophisticated delivery ability required for effective ventilation therapy. For example, U.S. Pat. No. 4,928,683 describes a closed line anesthesia respiratory apparatus using multiple fixed volume fluid driven compartments. While delivering precise volumes, this complex fixed delivery system does not provide the sophisticated profiles and versatility necessary for extended ventilation therapy. Moreover, the disclosed apparatus is not modular and compatible with off-the-shelf equipment. Similarly, U.S. Pat. No. 5,119,810 provides a ventilation system driven by a mechanical powered piston. Yet, this system does not allow for the use of existing ventilation apparatus and does not isolate the mechanical components from the respiratory gas. As such, neither of the disclosed devices solve the aforementioned problems. Thus, there still remains a great need for a closed-circuit ventilation system which allows for the isolation and retention of respiratory material.

Accordingly, it is an object of the present invention to provide methods and apparatus for closed-circuit pulmonary ventilation.

It is another object of the present invention to provide methods and apparatus for the efficient retention of a respiratory promoter during partial liquid ventilation.

It is yet another object of the present invention to provide methods and apparatus for the retention of a respiratory promoter during total liquid ventilation.

SUMMARY OF THE INVENTION

These and other objectives are achieved by the present invention which, in a broad aspect is directed to methods and apparatus for closed-circuit ventilation. More specifically, the present invention provides novel methods and devices for conducting ventilation using modular closed-circuit ventilation systems that prevent the unintentional loss of valuable materials, including fluorochemicals, into the environment. As used herein the term "ventilation" will be held to mean airflow in the lungs. Accordingly, the term "ventilation therapy" broadly means any procedure, including the administration of any therapeutic or diagnostic agent, that comprises airflow in the lungs. As such, ventilation therapy may be used in connection with both systemic and pulmonarily localized conditions.

The methods and apparatus of the present invention may be used with any type of ventilation including, but not limited to, conventional gas ventilation, partial liquid ventilation and total liquid ventilation. Similarly, the methods and devices of the present invention may be used with any gas, vapor or liquid to effect ventilation therapy including, but not limited to, non-anesthetic gases and vapors, bioactive agents including breathing gases, respiratory promoters including liquid breathing agents, (particularly fluorochemicals) and pharmaceutical agents. In sort the present invention of any gas, liquid or vapor optionally comprising a bioactive agent. Further, combinations of materials, such as the delivery of pharmaceutical agents in conjunction with a respiratory promoter are compatible with the present invention.

Another major advantage is that the closed-circuit ventilation systems of the present invention may be operably associated with conventional open-circuit mechanical ventilators to provide sophisticated controls and sensors desirable in extended ventilation therapy. Moreover, the closed-circuit devices of the present invention may be used to isolate delicate and relatively expensive mechanical ventilators from potentially damaging chemicals often employed in liquid ventilation procedures. This component isolation could greatly facilitates the regulatory process inherent in getting new ventilators approved for existing therapies. Further, as the devices of the present invention are modular, overall configurations and associated conventional devices, particularly ventilators, nebulizers, sensors and the like may be easily substituted or changed depending on therapeutic requirements or physician preferences. In addition, as the closed-circuit ventilation systems of the present invention may be fabricated from reliable, yet cost effective materials they may be designed to be disposable substantially reducing operating costs in terms of personnel and maintenance.

In a preferred embodiment, the invention provides a process for closed-circuit ventilation therapy comprising the steps of:

a) introducing at least one non-anesthetic gas or vapor into pulmonary air passages of a respiring patient;

b) capturing expiratory gas from said patient in a closed-circuit respirator in fluid-conducting communication with said pulmonary air passages, said expiratory gas comprising carbon dioxide and at least a portion of said introduced gas or vapor;

c) circulating said expiratory gas through a gas flow path defined by said closed-circuit respirator wherein at least a portion of said carbon dioxide is removed; and d) thereafter reintroducing at least a portion of the circulated expiratory gas comprising said introduced gas or vapor into the pulmonary air passages of the patient.

Preferably the non-anesthetic gas or vapor is a bioactive agent other than oxygen or air. In other preferred embodiments, the introduced gas or vapor is a respiratory promoter and, in particularly preferred embodiments a liquid breathing agent (for example, a fluorochemical) capable of transporting oxygen. In other embodiments at least a portion of the gas flow path may be pressurized to effect positive pressure ventilation of the patient with this pressure preferably provided by a mechanical ventilator. In yet other embodiments of the process, the closed-circuit respirator may comprise a variable volume reservoir that may be externally pressurized to provide positive pressure ventilation. The variable volume reservoir may comprise an isolation chamber bifurcated by a gas impermeable compliant membrane, with the compliant membrane separating the chamber into the variable volume reservoir in fluid-conducting communication with the pulmonary air passages and a compression reservoir in fluid communication with a conventional open-circuit ventilator. In such embodiments the open-circuit ventilator may be isolated from the circulating respiratory promoter.

In another broad aspect of the present invention, a modular apparatus for closed-circuit ventilation therapy is provided. In a preferred embodiment, the apparatus comprises:

a) a patient-connector capable of establishing fluid-conducting communication with pulmonary air passages of a patient;

b) a variable volume reservoir;

c) a ventilating conduit sealingly affixed to said patient-connector and said variable volume reservoir wherein said patient-connector is placed in fluid-conducting communication with said variable volume reservoir to provide a closed-circuit respirator defining a gas flow path; and d) a carbon dioxide separator in fluid-conducting communication with said gas flow path.

Selected exemplary embodiments of the present invention further include a variable volume reservoir comprising an isolation chamber bifurcated by a gas impermeable compliant membrane, said compliant membrane separating the chamber into a compression reservoir and said variable volume reservoir, with the variable volume reservoir in fluid-conducting communication with the pulmonary air passages. In such embodiments a conventional mechanical ventilator may be operably associated with the compression reservoir of the isolation chamber whereby normal operation of the ventilator will transmit a pressure wave to actuate the compliant membrane. As with direct ventilation systems (where the ventilator is in fluid-conducting communication with the patient) the transmitted pressure wave may be used to provide positive pressure ventilation. Yet, in these embodiments, unlike prior art systems, the gas transmitting the wave from the ventilator is never in contact with the pulmonary air passages.

In another preferred embodiment, an apparatus for closed-circuit ventilation is provided comprising a) a patient-connector capable of establishing fluid-conducting communication with pulmonary air passages of a patient;

b) a ventilating conduit sealingly affixed to said patient-connector to provide a closed-circuit respirator defining a gas flow path, said closed-circuit respirator operably associated with a mechanical ventilator; and c) a carbon dioxide separator in fluid-conducting communication with said gas flow path.

In yet another embodiment of the present invention, methods for providing closed-circuit partial liquid ventilation are provided. These methods generally comprise:

a) connecting an exogenous closed-circuit respirator defining a gas flow path to the pulmonary air passages of a respiring patient;

b) introducing a respiratory promoter into said pulmonary air passages;

c) capturing expiratory gas from said patient in said closed-circuit respirator, said expiratory gas comprising carbon dioxide and at least a portion of said introduced respiratory promoter;

d) separating said at least a portion of carbon dioxide to provide a treated gas comprising said respiratory promoter; and e) reintroducing said treated gas into the pulmonary air passages of the patient.

Preferably the respiratory promoter is a liquid breathing agent such as a fluorochemical, capable of transmitting oxygen. Moreover, embodiments of this method may further include the step of administering a respiratory promoter to the pulmonary air passages of the patient prior to establishing fluid-conducting communication between the present invention and the pulmonary air passages. It will further be appreciated that the disclosed partial liquid ventilation methods may further comprise pressurizing a portion of the gas flow path to effect positive pressure ventilation of the patient, preferably using pressure provided by a mechanical ventilator. Other exemplary embodiments of the process comprise a variable volume reservoir connected to the closed-circuit respirator. Any such reservoir may be externally pressurized (outside the closed-circuit respirator) to provide positive pressure ventilation.

The present invention also provides methods and devices for closed-circuit total liquid ventilation. In one embodiment the method comprises:

a) establishing fluid-conducting communication between pulmonary air passages of a patient and a fluid flow path defined by a closed circuit-liquid respirator, said fluid flow path and said pulmonary air passages substantially filled with a circulating liquid respiratory promoter;

b) oxygenating the circulating liquid respiratory promoter by introducing oxygen into the closed-circuit liquid respirator to provide oxygenated liquid respiratory promoter;

c) circulating oxygenated liquid respiratory promoter through the fluid flow path and said pulmonary air passages to provide expiratory fluid comprising carbon dioxide;

d) separating at least a portion of said carbon dioxide from the circulating expiratory fluid to provide inspiratory fluid.

In preferred embodiments the method will employ a second closed-circuit vapor separator designed to remove carbon dioxide from a gaseous vapor before introducing the treated vapor back into the circulating liquid respiratory promoter for reintroduction to the patient. In other preferred embodiments, a liquid scrubbing means will be placed in the fluid flow path to remove carbon dioxide directly from the circulating liquid respiratory promoter prior to reintroduction into the pulmonary air passages of the patient. Novel apparatus are also provided to perform the unique total liquid ventilation procedures disclosed herein.

In still another embodiment the present invention may comprise a method of operating a closed-circuit ventilation apparatus by pressurizing a closed-circuit respirator in fluid conducting communication with pulmonary air passages of a patient to effect positive pressure ventilation. In preferred embodiments the pressurizing step may be achieved by operating a conventional mechanical ventilator operably associated with the closed-circuit respirator while isolated from the pulmonary air passages.

Yet other embodiments of the present invention comprise treating fluid, gaseous or vaporous material from the lung of a patient by circulating the material through a closed-circuit respirator while removing waste gases and introducing oxygen. Preferably the material is removed from the lung by effecting positive pressure ventilation.

Other objects, features and advantages of the present invention will be apparent to those skilled in the art from a consideration of the following detailed description of preferred exemplary embodiments thereof taken in conjunction with the figures which will first be described briefly.

DETAILED DESCRIPTION OF THE PREFERRED EMBODIMENTS

While the present invention may be embodied in many different forms, disclosed herein are specific illustrative embodiments thereof that exemplify the principles of the invention. It should be emphasized that the present invention is not limited to the specific embodiments illustrated.

Conventional prior art mechanical ventilators, used for both partial liquid ventilation and traditional gas ventilation are open-circuit ventilators meaning that waste gases, such as carbon dioxide are vented into the environment. Total liquid ventilation devices used today are also open-circuit devices in that the waste gases (again primarily carbon dioxide) are vented into the environment following their separation from the liquid respiratory promoter used to improve gas exchange in the lung. In complete contrast to such prior art "open-circuit" designs, the present invention is directed to methods and devices which are used for "closed-circuit" ventilation wherein gases are not generally vented into the surrounding environment but rather treated and returned to the patient. As used herein, the term closed-circuit is held to mean any substantially closed system that allows the retention of the majority of incorporated materials circulating therein. More particularly, the exhaled gases or vapors (or liquid in the case of total liquid ventilation) from the patient are to remove waste products such as carbon dioxide and returned to the patient. In procedures involving liquid ventilation, this treatment and recirculation of the exhaled gases, vapors or liquids substantially reduces the amount of respiratory promoter needed to provide effective ventilation. In traditional gas ventilation, the closed-circuit methods and devices of the present invention can reduce the loss of any incorporated gas or vapor or bioactive agent including those having pharmaceutical efficacy such as therapeutic or diagnostic agents.

Pursuant to this disclosure, respiratory gas exchange may be maintained by continuous positive pressure ventilation using a conventional ventilator. By "continuous positive pressure ventilation" is meant positive pressure mechanical ventilation, often with positive end-expiratory pressure, and may be accomplished by any standard positive pressure ventilator. Either volume regulated, time-cycled respirators or pressure-limited time-cycled respirators are suitable. Examples of commercially available ventilators that are compatible with the present invention include, but are not limited to, Servo 900C (Seimens Elema, Shaumburg, Ill.), Infant Star (Star Products, San Diego, Calif.), Bear 1,2,3 (Bear Medical, Browns, Calif.), Puriton Bennett 7200, (Puriton-Bennett Corp., Carlsbad, Calif.) Baby Bird 2 (Bird Corp., CA), and the Healthdyne Infant Ventilator. As previously alluded to, conventional ventilators such as these may be used with the present invention in conjunction with traditional gas ventilation or with partial liquid ventilation.

Figure 1:
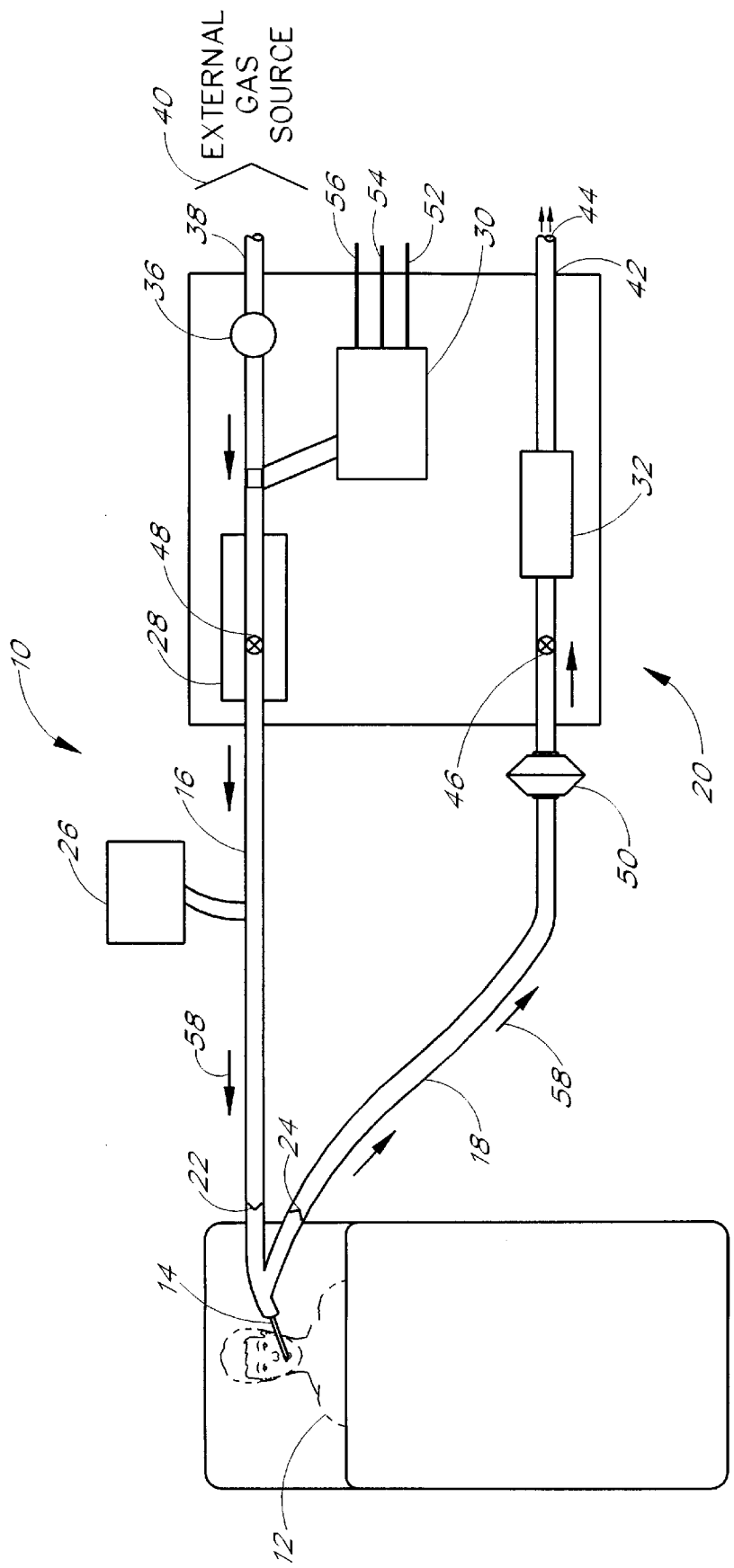
FIG. 1 is a schematic representation of a conventional open-circuit mechanical ventilation system.

FIG. 1 provides a schematic representation of a conventional "open-circuit" mechanical ventilation system 10 illustrating the principal features thereof. In the figure, mechanical ventilation system 10 is connected to a patient 12 through a patient-connector 14. Typically, patient-connector 14 will comprise an endotracheal tube or a mask that allows gas, vapors and liquids to be administered to the lungs of the patient. In the apparatus shown, the distal end of patient-connector 14 branches to form a Y-connector providing two separate distal connecting ports. The distal connecting ports are sealingly attached to the proximal ends of inspiratory ventilating conduit 16 and expiratory ventilating conduit 18 respectively. For the purposes of this application the terms "conduit" or "ventilating conduit" will be held to mean any hose, tube, bore, lumen, shaft or other void containing structure capable of defining a fluid flow path. Those skilled in the art will appreciate that exemplary inspiratory ventilating conduit 16 and expiratory ventilating conduit 18 are typically formed of biocompatible flexible tubing having annular reinforcements to prevent kinking or blockage. Moreover, such ventilating conduits may be formed of materials compatible with specific respiratory promoters. Inspiratory ventilating conduit 16 defines a gas flow path comprising a gas flow path or bore which is capable of transporting gas to patient-connector 14 where it is administered to the pulmonary air passages. Similarly, expiratory ventilating conduit 18 defines a gas flow path that may be used to transport expiratory gas away from said patient upon exhalation. Arrows 58 illustrate the flow of gas through the system.

As with all commercially available mechanical ventilators, mechanical ventilation system 10 relies on pressurized gas source 40 for pneumatic power. In conventional mechanical ventilators pressurized gas source 40 is provided by an external bulk gas delivery system (i.e. pressurized tanks) or an internal compressor (not shown) which pressurizes air from the surrounding environment. In either case, pressurized air enters mechanical ventilation system 10 through inlet conduit 38 and pressure regulator. Although air from the pressurized gas source is typically on the order of 50 lb/in$^2$, pressure regulator 36 reduces this to a working pressure of approximately 1.5 lb/in$^2$ prior to employing it in mechanical ventilation system 10. Following the reduction of pressure the gas enters the distal or upstream end of inspiratory ventilating conduit 16.

Ventilating conduits 16 and 18 are operably associated with conventional mechanical ventilator apparatus 20. By "operably associated" it is meant that gas flow and ventilation operations using conduits 16 and 18 may be controlled, monitored and effected by ventilator apparatus 20. To this end ventilator apparatus 20 comprises inspiratory sensor assembly 28 and expiratory sensor assembly 32 which monitor and control gas flow and/or gas composition through inspiratory ventilating conduit line 16 and expiratory ventilating conduit line 18 respectively. Among other data, sensor assemblies 28 and 32 provide real time information regarding gas composition, temperature, pressure and flow rate. Accordingly, gas entering inspiratory ventilating conduit 18 is monitored by inspiratory sensor assembly 28. Based on the readings, gas injector 30 may be signaled or manually set to introduce oxygen or other gases to the gas flow path defined by inspiratory ventilating conduit 18. Transfer lines 52, 54, 56 provide gas injector 30 with access to external sources of oxygen, nitrogen or other selected gases. Those skilled in the art will appreciate that gas injector 30 may operate using preprogrammed instructions or may be controlled by ventilator apparatus 20 based on information from sensor assemblies 28 and 32 or using preset values.

Gas flow and pressure through conduits 16 and 18 is physically controlled through inspiratory flow valve 48 and optional expiratory flow valve 46 which are opened and closed based on preprogrammed instructions and information received from sensor assemblies 28 and 32. Those skilled in the art will appreciate that flow valves 46 and 48 may comprise any of a number of different types of valves including solenoid valves, digital solenoid valves and full-range proportional valves. As will be described below, flow valves 46 and 48 will be manipulated to provide the desired wave form and pressure for ventilation. Passing downstream through inspiratory flow valve 48 the inspiratory gas may be modified by humidifier 26 which introduces vapor to the gas flow path. As with gas injector 30, humidifier 26 may be controlled by preprogrammed instructions manual settings or by ventilator apparatus 20. The inspiratory gas, now containing adequate oxygen and water vapor is then transported along the gas flow path through one arm of patient-connector 14 and into patient 12. Optional inspiratory check valve 22 may be provided to ensure the directional travel of the inspiratory gas.

Preferably the inspiratory flow pattern is manipulated to provide optional ventilation for the patient. That is, the wave form and pressure of the delivered gas may be optimized to minimize pulmonary resistance and maximize pulmonary compliance. As previously indicated, ventilator apparatus 20 may be classified as either a pressure, volume, flow or time controller device. If the pressure waveform does not change with changes in patient resistance and compliance, then the ventilator is considered a pressure controller. Conversely, if the delivered volume is measured directly, then the ventilator is considered a volume controller. If the delivered volume is determined by a flow transducer, then the ventilator is a flow controller. Finally if both pressure and volume wave forms change with changes in patient resistance and compliance, then the ventilator is considered a time controller. Most commercially available mechanical ventilators are either pressure, volume or flow controllers. It is primarily this ability to provide sophisticated delivery patterns, and monitor and react to the changing conditions, that differentiate ventilators from other gas delivery devices such as anesthesia machines.

Whatever delivery mode is used to introduce the inspiratory gas to the pulmonary air passages (not shown) of patient 12 under positive pressure, ventilation is effected upon distribution of the gas in the lungs to promote gas exchange and oxygenation. Those skilled in the art will appreciate that the fresh oxygen from the introduced inspiratory gas crosses the alveoli and enters the blood while waste gases (carbon dioxide, etc.) are excreted from the body. As described in Fuhrman, U.S. Pat. No. 5,437,272, published PCT Application No. WO 92/19232, and co-pending U.S. patent application Ser. No. 08/180,700 all incorporated herein by reference, a respiratory promoter (preferably comprising a fluorochemical) may be present in the pulmonary passages of patient 12 to facilitate the uptake of oxygen and excretion of waste gases. As oxygen passes into the bloodstream, waste gases simultaneously collect in the lungs. When using conventional mechanical ventilators, such as the one shown in FIG. 1, the introduction of inspiratory gas will typically be pulsed or cycled. This introductory period is known as the inspiratory phase of the breathing cycle. During the lull between the introduction of gases, the lungs return to ambient pressure and deflate due to tension on pulmonary passages from surrounding tissue. This contraction of the lungs and corresponding reduction in lung volume forces accumulated gases and vapors, collectively known as expiratory gas, from the lungs. This form of expiration is termed spontaneous exhalation. In the case of traditional gas ventilation the expiratory gas will comprise unused oxygen and waste gases including carbon dioxide. When a respiratory promoter has been introduced into the lung of the patient, such as when performing PLV, the expiratory gas will comprise vaporized respiratory promoter in addition to unrespired oxygen and waste gases.

The spontaneous contraction of the lungs forces the expiratory gas into patient-connector 14, preferably sealingly connected to patient 12. Unidirectional inspiratory check valve 22 prevents the expiratory gas from substantially entering inspiratory ventilating conduit 16. Instead the expiratory gas is directed through unidirectional expiratory check valve 24 into expiratory ventilating conduit 18. From here the expiratory gas travels along the gas flow path defined by expiratory ventilating conduit 18, through optional flow control valve 46, and into ventilator apparatus 20. Optionally, the expiratory gas may be passed through filter 50, positioned anywhere along expiratory ventilating conduit 16, wherein pathogenic organisms and other undesirable material may be removed from the expiratory gas. After entering ventilator apparatus 20 the gas flow passes through sensor assembly 32 wherein data may be gathered regarding the composition and flow of the expiratory gas as well as the breathing cycle. Those skilled in the art will appreciate that the schematic representation of the sensors in FIG. 1 is exemplary only and that any sensors employed in ventilator apparatus 20, including those compatible with the present invention may collect the desired information using any effective means. Passing through ventilator apparatus 20 in the gas flow path defined by expiratory ventilating conduit 18 the expiratory gas proceeds through outlet conduit 42 and is vented into the surrounding environment through exhaust aperture 44. It is this venting into the surrounding atmosphere that classified systems as "open."

Figure 2:
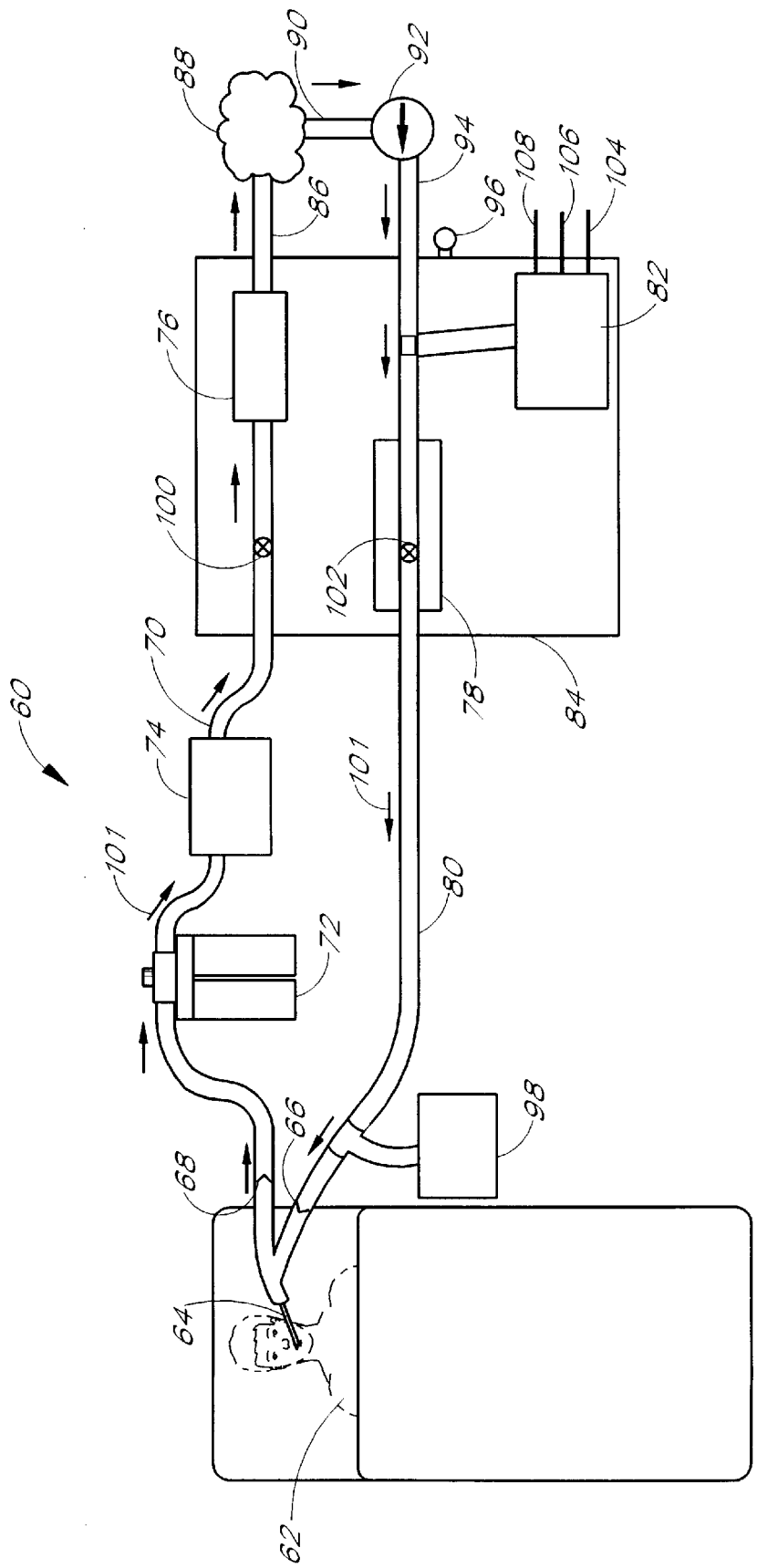
FIG. 2 is a schematic representation of an exemplary closed-circuit ventilating system formed in accordance with the teachings of the present invention.

In contrast to the "open-circuit" ventilation system depicted in FIG. 1, FIG. 2 schematically illustrates a "closed-circuit" positive pressure ventilation system of the present invention. More particularly, FIG. 2 depicts a closed-circuit ventilation system that allows treated expiratory gas to be returned to the patient. As used herein, the term closed-circuit is held to mean any substantially closed system that allows the retention of the majority of incorporated materials circulating through the system. Unlike the conventional apparatus shown in FIG. 1, no external source of pressurized air is required for the closed-circuit system of the present invention. As discussed above, returning the treated gases (including vapors therein) to the patient avoids the loss of valuable gases or vapors, including respiratory promoters such as bioactive agents or fluorochemicals, to the environment and minimizes the spread of pathogens. Advantageously, this closed-circuit system employs a mechanical ventilator that is substantially the same as the one illustrated in FIG. 1. In actuality, the incorporated ventilator apparatus may be a suitably modified conventional mechanical ventilator or may be one specifically built to embody the closed-circuit design. In either case, control and operation of the novel closed-circuit system could be made similar enough to conventional open-circuit ventilation systems to promote operator familiarity and acceptance.

More specifically, the gas flow path of FIG. 2 (shown by arrows 101) is defined by a closed-circuit respirator comprising patient-connector 64, ventilating conduits 70, 86, 90, 94, 80 and carbon dioxide separator 72. As used herein, "closed-circuit respirator" is held to mean that portion of the closed-circuit ventilation system defining the primary flow path of whatever vapor, gas, or fluid is being used for the ventilation procedure. That is, the selected material or compound is substantially confined to this closed-circuit respirator as it is recirculated in and out of the pulmonary air passages. Optionally, the closed-circuit respirator may comprise variable volume reservoir 88 and be in fluid-conducting contact with gas injector 82 and nebulizer 98. The gas used for ventilation, treated to remove carbon dioxide and periodically supplemented with oxygen, is repeatedly circulated through this gas flow path during the duration of the respiratory therapy. This is completely different from the open-circuit ventilation system of FIG. 1 where the ventilating gas is used once and discarded without any treatment whatsoever. In the present invention, components of the ventilation gas other than carbon dioxide and oxygen rapidly reach an equilibrium throughout the closed-circuit respirator and the pulmonary air passages. This equilibria is very easy to maintain, requiring minimal addition of those elements (other than oxygen) which are being circulated. Even the addition of oxygen is reduced to what the body has actually used rather than what is discarded in traditional systems. Accordingly, the closed-circuit ventilation systems of the present invention are much cheaper and more efficient to operate, particularly when expensive materials such as fluorochemicals or pharmaceutical agents are incorporated in the therapeutic regimen.

As with the conventional ventilation system of FIG. 1, FIG. 2 shows patient 62 connected to closed-circuit ventilation system 60 via patient-connector 64. Preferably, patient-connector 64 (typically an endotracheal tube or mask) sealingly provides fluid-conducting communication between closed-circuit ventilation system 60 and the pulmonary air passages (not shown) of patient 62. As discussed above, inspiratory gas is forced into the lungs of patient 62 using pulsed or cyclical positive pressure. Following respiration, expiratory gas is forced from the lung under pressure during spontaneous exhalation and passes through branched patient-connector 64. Unidirectional inspiratory check valve 66 prevents the exhaled expiratory gas from entering the gas flow path defined by inspiratory ventilating conduit 80, directing it instead through unidirectional expiratory check valve 68 and into the gas flow path defined by expiratory ventilating conduit 70. While two separate ventilating conduits are used in this embodiment, those skilled in the art will appreciate that many different configurations of conduit are acceptable being limited only by their ability to transport the necessary material. The expiratory gas may be may be moved along the gas flow path by the pressure of the exhalation, by negative pressure (sucking) provided by gas moving apparatus 92 or by a combination of both. In any case, the expiratory gas travels through expiratory ventilating conduit 70 and enters carbon dioxide separator 72 which is sealingly connected in fluid-conducting communication with the defined gas flow path.

Preferably, the materials used in the closed-circuit respirator are compatible with any respiratory promoter. Particularly preferred fabrication materials are generally compatible with fluorochemicals. In particular, such materials include, but are not limited to Cellulose acetate +, Polypropylene, Polyurethane, Polyethylene, HDPE, Polyvinylidene difluoride, Stainless Steel, Teflon FEP, Teflon PTFE, Teflon, Viton, Viton A, Acrylic, Brass, chrome-plated, Cycolac ABS, Polyvinyl chloride, Polyvinylidene difluoride +, Rubber, Polycarbonate, Polyester, and High density polyethylene.

Carbon dioxide separator 72 is used to remove at least a portion of the carbon dioxide from the expiratory gas. Essentially it is a device which chemically or physically binds carbon dioxide and removes it from the gas flow path. In preferred embodiments, carbon dioxide separator 72 comprises one or more canisters containing a material such as soda lime, sodium hydroxide or lithium hydroxide in a solid form. As the expiratory gas, comprising unrespired oxygen, carbon dioxide and any respiratory promoter passes through the canisters, the carbon dioxide reacts with the base to form a carbonate on the exposed surface and water. This reaction removes the carbon dioxide from the gaseous phase. Those skilled in the art will appreciate that such carbon dioxide separator, generally reusable, are commercially available in a variety of forms. As such, various configurations, models and types of carbon dioxide separator are compatible with the present invention and may be used in accordance with the teachings herein.

In FIG. 2 the treated expiratory gas (with lower carbon dioxide levels) exits carbon dioxide separator 72 and passes through expiratory ventilating conduit 70 to optional vapor analyzer 74. It must be emphasized that the embodiment shown is exemplary only and that carbon dioxide separator 72 and vapor analyzer 74 may be placed anywhere along the gas flow path defined by the closed-circuit respirator. Wherever it is placed, optional vapor analyzer 74 may be used to supplement the sensors provided in ventilator apparatus 84. In particular, vapor analyzer 74 may comprise means for determining the amount and composition of any vaporized respiratory promoter present in the gas flow path during partial liquid ventilation. Of course vapor analyzer 74 may be used to provide information regarding other vapors in the gas, i.e. water vapor, as well as general parameters of the gas. Accordingly, it may be used to compliment other sensors or in lieu of other sensors. In preferred embodiments, data from vapor analyzer 74 may be fed to ventilator apparatus 84 or to optional nebulizer 98 to regulate the amount of circulating vaporized respiratory promoter in the gas flow path. In this embodiment the treated and analyzed expiratory gas continues through expiratory ventilating conduit 70, through any expiratory sensor assembly 76 in ventilator apparatus 84 and passes into outlet ventilating conduit 86. As described previously, optional expiratory flow control valve 100 may be used to control the flow and pressure of the gas.

In direct contrast to conventional open-circuit mechanical ventilators, the gas is not vented into the surrounding environment following passage through outlet conduit 86 but rather, is directed into variable volume reservoir 88. Variable volume reservoir 88 acts as a pulse damping mechanism and gas reservoir to ensure the smooth flow of gas throughout the gas flow path defined by the closed-circuit respirator. In preferred embodiments variable volume reservoir may comprise a balloon-like device or bellows. In other embodiments, the reservoir may be a compliant gas impermeable membrane which expands and contracts with variations in the pressure of the gas in the defined flow path. The treated expiratory gas is sucked from variable volume reservoir 88 and through transfer ventilating conduit 90 by gas moving apparatus 92 which is in fluid-conducting contact with the gas flow path. Preferably gas moving apparatus 92 is a low pressure (on the order of 1.5 lb/in$^2$ or less) pump or blower capable of circulating the gas through the gas flow pipe. The effect of the generated negative pressure on expiratory ventilating conduit 70 may be regulated by expiratory flow control valve 100. While high pressure (on the order of 60 lb/in$^2$ or more) pumps may be used as gas moving apparatus 92, the increase in pressure may condense vaporized respiratory promoter present in the gas flow path. Accordingly, low pressure pumps or blowers which maintain the phase equilibria of the ventilating gas are desirable.

Gas moving apparatus 92 propels the treated expiratory gas through inlet conduit 94 and into ventilator apparatus 84. In the embodiment shown, ventilator apparatus 84 is representative of a commercially available open-circuit mechanical ventilator which has been modified in accordance with the present invention. Accordingly, pressure regulator 96, necessary on open-circuit configurations employing a high pressure external gas source is bypassed in the embodiment shown. Other exemplary modifications of such systems could include incorporation of fluorochemical compatible materials along the gas flow path. While FIG. 2 is representative of a modified conventional mechanical ventilator, it should be emphasized that a ventilator apparatus analogous to that shown may be specifically designed for closed-circuit ventilation therapy. In such a device the high pressure regulator would be omitted entirely.

Upon introduction to ventilator apparatus 84, the gas enters inspiratory ventilating conduit 80. As discussed above, gas injector 82 is in fluid-conducting communication with the gas flow path defined by inspiratory ventilating conduit 80 and may introduce oxygen, nitrogen or other gases supplied by lines 104, 106, 108 to the gas flow path. Since unrespired oxygen is present in the circulating gas, the closed-circuit configurations of the present invention allow effective respiratory therapy with much less input of oxygen and other supplemental gases. Essentially, it is only the gases which are actually used by the body that must be replace in the ventilation gas. This is in sharp contrast to open-circuit ventilator systems where the external air must consistently be supplemented. Gas flow continues through inspiratory ventilating conduit 80 past inspiratory sensor assembly 78 where gas flow, pressure and composition are measured as discussed above. Data from inspiratory sensor assembly 78 is preferably used to control gas injector 82 and inspiratory flow control valve 102 allowing gas flow to be modified. Pressured by gas moving apparatus 92, the inspiratory gas transverses the gas flow path defined by inspiratory ventilating conduit 80, passes optional nebulizer 98, and enters the pulmonary air passages of patient 12 through unidirectional inspiratory check valve 66 and patient-connector 14 to effect positive pressure ventilation. Reintroduced with the inspiratory gas is at least a portion of any respiratory promoter previously present in the pulmonary air passages. That is, the respiratory agent or liquid medium has been recirculated.

Optional nebulizer 98 is in fluid-conducting communication with the gas flow path defined by inspiratory ventilating conduit 80. As used herein "nebulizer" will mean any type of nebulizer, humidifier or vaporizer which may be used to deliver particulate or vaporized material to the gas flow path. While positioned along inspiratory ventilating conduit 80 in FIG. 2, nebulizer 98 may be placed anywhere along the closed-circuit defining the gas flow path. Those skilled in the art will appreciate that nebulizer 98 may be used to introduce aerosols, mists, sprays, vapors, powders or combinations thereof into the gas flow path thus maintaining compositional equilibria of the ventilating gas or adding respiratory agents. Normally nebulizer 98 is activated only during the inspiratory phase without affecting the delivered tidal volume or inspired oxygen. In particular, nebulizer 98 may be used to deliver liquid medium, preferably fluorochemicals, to the gas flow path for partial liquid ventilation. In especially preferred embodiments, nebulizer 98 is used to provide fluorochemicals, heated above body temperature, to the ventilating gas in the form of a vapor. This may be accomplished by spraying or contacting a wetted surface or wick with the gas to form droplets. In this form, the fluorochemical liquid medium is particularly well dispersed in the lungs. As the fluorochemical vapor cools in the body it is deposited on the pulmonary surfaces to assist in gas exchange and oxygenation. In addition to nebulizer 98, the gas flow path may further contain heating means such as a wick or electric elements in the ventilating conduit to prevent condensation of the respiratory promoter and water.

It should be emphasized that the present invention is particularly useful when used in conjunction with liquid ventilation and especially partial liquid ventilation. Partial liquid ventilation has a number of benefits over conventional gas ventilation. The lungs are bathed in a biocompatible fluid. Lung trauma is minimized and this permits lung maturation and repair. Partial liquid ventilation is more amenable to use than total liquid breathing since air or gas can still be inhaled and exhaled. Partial liquid ventilation can be used in conjunction with spontaneous, passive or mechanical ventilation in accordance with the present invention and, because it is more natural, precludes the necessity of deep sedation and/or paralysis of respiratory muscles. In addition, pharmacologic substances can be added to the fluorochemical to further promote resolution of pulmonary and systemic disorders.

Performing PLV in accordance with the present invention may comprise the administration of very low doses (on the order of 0.01 ml/kg or less) of the desired fluorochemical or combination of fluorochemicals. Essentially, a therapeutically effective amount comprises enough to form a thin coating on a portion of the lung. Conversely, the level of fluorochemical in the lung may actually exceed the functional residual capacity of the patient. That is, the amount of fluorochemical used for partial liquid ventilation may approximate the volume of air remaining in a healthy lung of similar size following exhalation, or alternatively, that volume plus the volume of the endotracheal tube. The actual volumes will depend on the treatment protocol, the weight and size of a patient, as well as the lung capacity. While not limiting the scope of the present invention to any one mechanism, it is believed that the remarkably low surface tension of biocompatible fluorochemicals alters the mechanical behavior of the respiratory system during partial liquid ventilation. Observed changes in respiratory mechanics suggests that, following the pulmonary introduction of low doses of a fluorochemical, a thin film of FC with a low surface tension is formed due to evaporation and covers the interior of the lung. This fluorochemical film reduces surface tension at the alveolar air-liquid interface thereby facilitating lung expansion and increasing oxygen availability.

Thus, during partial liquid ventilation in accordance with the present invention, the lungs retain sufficient air capacity (above and beyond the volume of fluorochemical in the lung) to permit inhalation such that normal breathing can proceed. The amount of air entering the lungs on inhalation is sufficient to oxygenate the fluorochemical liquid. Further, the fluorochemical liquid may be oxygenated prior to use to provide oxygen to the alveolar surfaces of the lung instantaneously upon initial contact with the fluorochemical.

In a particularly preferred embodiment of the present invention the desired amount of fluorochemical is administered to the lung and the closed-circuit ventilation apparatus is attached. Respiratory therapy is begun, preferably with positive pressure ventilation, with the atmosphere in the lung and the closed-circuit respirator defining the gas flow path quickly becoming saturated with fluorochemical. Oxygen and small amounts of fluorochemical are added to maintain the desired environment while the recirculated ventilating gas is treated to remove carbon dioxide. Preferably, the process is monitored by sensors in the respirator apparatus and a vapor analyzer is used to control the amount of fluorochemical added to the closed-circuit system. Following completion of the therapy the system is removed and the fluorochemical is allowed to evaporate.

In another preferred embodiment, the aforementioned process is carried out without the preliminary administration of fluorochemical to the lung. Rather the liquid medium is added to the closed-circuit system, preferably in a nebulized or vaporized form. Again the environment quickly reaches substantial equilibrium for the components of the ventilating gas other than carbon dioxide and oxygen. These levels are then easily maintained by small additions of material from the nebulizer and gas injector. This method is particularly preferred for PLV involving the pulmonary introduction of respiratory promoter at volumes less than functional residual capacity of the patient.

As discussed above, PLV may be undertaken using any liquid medium which provides the desired pulmonary therapeutic response. For example, in some indications hyperoxygenated saline may be used in accordance with the present invention. Preferably however, PLV will be performed using a fluorochemical. Particularly preferred embodiments employ fluorochemicals that are liquid at body temperature.

By "fluorochemical" is meant any fluorinated carbon compound with appropriate physical properties of biocompatibility. These properties are generally met by fluorochemicals having low viscosity, low surface tension, low vapor pressure, and high solubility for oxygen and carbon dioxide making them able to readily promote gas exchange while in the lungs. For example, it is preferred that the fluorochemical have at least 3 or 4 carbon atoms and/or that its vapor pressure at 37° C. is less than 760 Torr. The fluorochemical may be made up of atoms of carbon and fluorine, or may be a fluorochemical having atoms other than just carbon and fluorine, e.g., bromine or other nonfluorine substituents. Those skilled in the art will appreciate that the range of compatible fluorochemicals is substantially broadened by the present invention.

More specifically, one of the major advantages of the present invention is that closed-circuit ventilation allows the extended therapeutic use of fluorochemicals that were previously too volatile to use effectively. Previously, some volatile fluorochemicals were used for short term drug therapy where pulmonary retention time was not critical. With the present invention, high vapor pressure fluorochemicals may be used effectively as they are not lost to the outside atmosphere. That is, the closed-circuit systems of the present invention promote substantial equilibrium for most ventilating gas components including volatile fluorochemicals. Accordingly, steady pulmonary levels of these fluorochemicals are rapidly reached and easily maintained using the novel closed-circuit systems described herein.

Preferably the selected fluorochemical will be able to cover a substantial amount of pulmonary tissue with relatively little volume. The ability of a given substance to cover a measured surface area can be described by its spreading coefficient. The spreading coefficients for fluorochemicals can be expressed by the following equation:

$$S(o \text{ on } w) = g_{w/a} - (g_{w/o} + g_{o/a})$$

Where S (o on w) represents the spreading coefficient; g=interfacial tension; w/a=water/air; w/o=water/oil; and o/a=oil/air.

Fluorochemicals exhibiting a positive spreading coefficient, will tend to spread over the respiratory membrane spontaneously. Fluorocarbons having spreading coefficients of at least one are particularly preferred. If the spreading coefficient is negative, the compound will tend to remain as a lens on the membrane surface. Adequate coverage of the lung surface is desirable for restoring oxygen and carbon dioxide transfer and for lubricating the lung surfaces to minimize further pulmonary trauma.

Representative fluorochemicals useful in the present invention include bis(F-alkyl) ethanes such as $C_4F_9CH{=}CH_4CF_9$ (sometimes designated "F-44E"), i-$C_3F_9CH{=}CHC_6F_{13}$ ("F-i36E"), and $C_6F_{13}CH{=}CHC_6F_{13}$ ("F-66E"); cyclic fluorochemicals, such as C10F18 ("F-decalin", "perfluorodecalin" or "FDC"), F-adamantane ("FA"), F-methyladamantane ("FMA"), F-1,3-dimethyladamantane ("FDMA"), F-di-or F-trimethylbicyclo [3,3,1]nonane ("nonane"); perfluorinated amines, such as F-tripropylamine("FTPA") and F-tri-butylamine ("FTBA"), F-4-methyloctahydroquinolizine ("FMOQ"), F-n-methyldecahydroisoquinoline ("FMIQ"), F-n-methyldecahydroquinoline ("FHQ"), F-n-cyclohexylpurrolidine ("FCHP") and F-2-butyltetrahydrofuran ("FC-75" or "RM101"). Brominated fluorochemicals include 1-bromo-heptadecafluoro-octane ($C_8F_{17}Br$, sometimes designated perfluorooctylbromide or "PFOB"), 1-bromopenta-decafluoroheptane ($C_7F_{15}Br$), and 1-bromotridecafluorohexane ($C_6F_{13}Br$, sometimes known as perfluorohexylbromide or "PFHB"). Other brominated fluorochemicals are disclosed in U.S. Pat. No. 3,975,512 to Long.

Also contemplated are fluorochemicals having nonfluorine substituents, such as perfluorooctyl chloride, perfluorooctyl hydride, and similar compounds having different numbers of carbon atoms.

Additional fluorochemicals contemplated in accordance with this invention include perfluoroalkylated ethers or polyethers, such as $(CF_3)_2CFO(CF_2CF_2)_2OCF(CF_3)_2$, $(CF_3)_2CFO$—$(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorochemicalhydrocarbon compounds, such as, for example, compounds having the general formula $C_nF_{2n+1}$—$C_{n'}F_{2n'+1}$, $C_nF_{2n+1}OC_{n'}F_{2n'+1}$, or $C_nF_{2+1}CF$=$CHC_{n'}F_{2n'+1}$, where n and n' are the same or different and are from about 1 to about 10 (so long as the compound is a liquid at room temperature). Such compounds, for example, include $C_8F_{17}C_2H_5$ and $C_6F_{13}CH$=$CHC_6H_{13}$. It will be appreciated that esters, thioethers, and other variously modified mixed fluorochemical-hydrocarbon compounds are also encompassed within the broad definition of "fluorochemical" liquids suitable for use in the present invention. Mixtures of fluorochemicals are also contemplated and are considered to fall within the meaning of "fluorochemical liquids" as used herein. Additional "fluorochemicals" contemplated are those having properties that would lend themselves to pulmonary gas exchange including FC-75, FC-77, RM-101, Hostinert 130, APF-145, APF-140, APF-125, perfluorodecalin, perfluorooctylbromide, perfluorobutyl-tetrahydrofuran, perfluoropropyl-tetrahydropyran, dimethyl-adamantane, trimethyl-bicyclo-nonane, and mixtures thereof. In particular, preferred fluorochemicals are characterized by having: (a) an average molecular weight range from about 350 to 570; (b) viscosity less than about 5 centipoise at 25° C.; (c) boiling point greater than about 55° C.; (d) vapor pressure in the range from about 5 to about 75 Torr, and more preferable from about 5 to about 50 Torr, at 25° C.; (e) density in the range of about 1.6 to about 2 gm/cm$^3$; and (f) surface tensions (with air) of about 12 to about 20 dyne/cm.

As previously indicated, the volume of fluorochemical liquid introduced into the pulmonary air passages should preferably be substantially equivalent to 0.01% to 100% of the normal pulmonary functional residual capacity (FRC) of the host. By "pulmonary functional residual capacity" is meant the volume of space in the pulmonary air passages at the end of expiration. For different applications, different amounts of fluorochemical are preferred. In one embodiment, the volume of fluorochemical liquid is at least 1%, 2%, 3% or 5% of the pulmonary FRC of the host. Preferably, the volume of fluorochemical liquid is at least 10% of the host's pulmonary FRC. In another embodiment, the volume of fluorochemical liquid is at least 20% of the pulmonary FRC of the host. In other preferred embodiments, the volume of fluorochemical liquid is not more than 30%, 50% or 75% of the host's pulmonary FRC. Alternatively, the volume of fluorochemical liquid is not more than 20% of the pulmonary FRC of the host. The normal pulmonary FRC of the host is calculated by methods well known in the art. It will be appreciated by those skilled in the art that preferred volumes of filling the lungs with fluorochemicals may be within certain ranges instead of discrete percentages. Thus, preferred embodiments of the invention include administration of fluorochemical of 0.01–1%, 0.01–10%, 1–10%, 1–20%, 5–50%, 10–70%, 50–75%, 50–100% and 75–100% of the host's pulmonary FRC, calculated using standard methods known in the art. Delivery of fluorochemical to a single lobe (unilateral) or local portion (lobar, segmental) is also contemplated.

Figure 3:
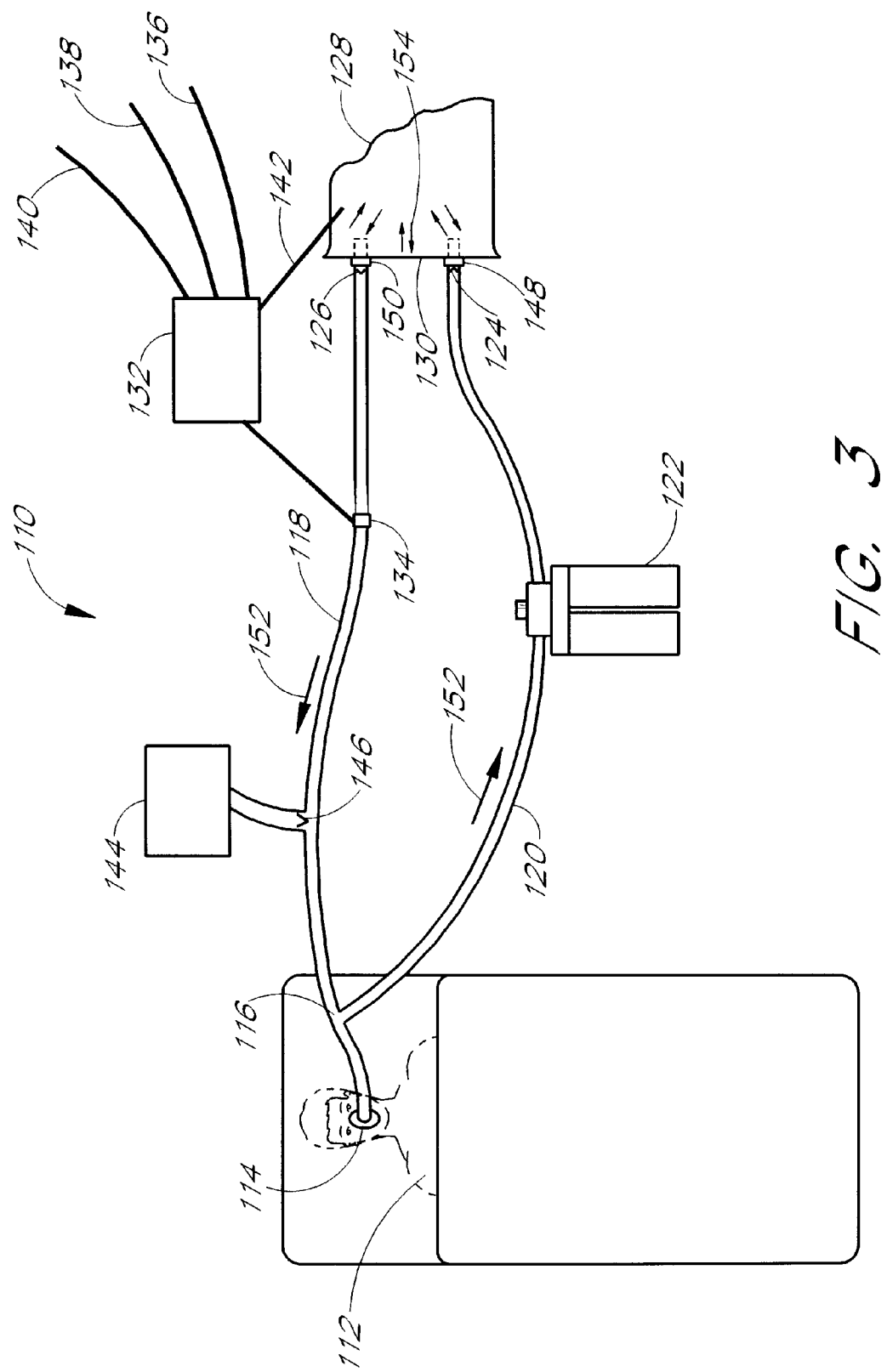
FIG. 3 is a schematic representation of an exemplary closed-circuit passive ventilation system incorporating an optional nebulizer.

An alternative embodiment of the closed-circuit ventilation systems of the present invention is schematically illustrated in FIG. 3. In the embodiment shown, the patient is undergoing passive ventilation meaning that no external pressure, other than that generated by the spontaneous respiration of the patient, is being put on the closed-circuit respirator. Accordingly, this embodiment is preferably used on patients requiring respiratory therapy but whose natural pulmonary function is strong enough for life support purposes. That is, for patients which do not require positive pressure ventilation. This embodiment may be used for both traditional gas ventilation comprising the administration of a respiratory agent and for partial liquid ventilation.

For example, this embodiment may be used in emergency situations or in the home where sophisticated mechanical equipment is impractical. Another favored use for the depicted embodiment would be for pulmonary drug therapy, with or without an adjunct liquid medium, such as for the administration of antibiotics in tuberculosis cases. The use of such a closed-circuit system would greatly reduce the chance of infection in care givers and fellow patients. Moreover, the closed-circuit ventilation apparatus depicted in FIG. 3 could be made, at least in part, from reliable yet inexpensive materials making it disposable, Specifically, the closed-circuit respirator defining the gas flow could be made of cost effective material allowing one readily dispose of it after disconnecting the more expensive and reusable equipment used for monitoring purposes. Conversely, the entire system could be made reusable.

Turning now in detail to the figure, closed-circuit ventilation system 110 is sealingly associated with patient 112 via patient-connector 114 establishing fluid-conducting communication between the pulmonary air passages (now shown) and the closed-circuit respirator. In this embodiment, patient-connector 114 comprises a proximal mask covering the mouth and nose of patient 112 and a distal Y-connector 116. Distal Y-connector 116 of patient-connector 114 is sealingly affixed to inspiratory ventilating conduit 118 and expiratory ventilating conduit 120. As discussed above, patient 112 is undergoing respiration comprising an inspiration phase and an expiration phase. However, unlike the embodiment of the present invention previously discussed, this respiration is spontaneous and does not require positive pressure ventilation of maintenance. Rather, the natural compression of the pulmonary cavity will provide the necessary pressure to force the gas through the gas flow path defined by the closed-circuit respirator.

Under spontaneous exhalation pressure the expiratory gas is forced through patient-connector and into expiratory ventilating conduit 120. Once again the expiratory gas comprises carbon dioxide, unrespired oxygen and, optionally, liquid medium or a respiratory agent. Ambient gas already in inspiratory ventilating conduit 18, and confined therein by unidirectional inspiratory check valve 126, will prevent substantial entry of the expiratory gas. Arrows 152 indicate the direction of gas flow through the closed-circuit respirator. Following entry into the proximal end of expiratory ventilating conduit 120, the expiratory gas passes through carbon dioxide separator 122 in fluid-conducting communication with the gas flow path defined by expiratory ventilating conduit 120. Upon interaction with carbon dioxide separator 122, at least a portion of the carbon dioxide in the expiratory gas is removed as previously explained. Following removal of the carbon dioxide, the treated expiratory gas is forced through unidirectional expiratory check valve 124 and annular connector 148 and exits the distal end of expiratory ventilating conduit 120 into variable volume reservoir 154.

In the illustrated embodiment variable volume reservoir 154 is defined by compliant membrane 128 and rigid member 130. Annular connectors 148 and 150 sealingly couple, respectively, expiratory ventilating conduit 120 and inspiratory ventilating conduit 118 to rigid member 130. Ventilating conduits 120 and 118 are attached to rigid member 130 adjacent to their distal ends. The distal ends of ventilating conduits 120 and 118 extend into variable volume reservoir 154 thereby establishing fluid-conducting communication between each individual ventilating conduit 118, 120 and variable volume reservoir 154. Of course, those skilled in the art will appreciate that the illustrated connectors are exemplary only and that any sealing connectors or configurations which establishes the desired fluid-conducting communication between the ventilating conduits and the variable volume reservoir is compatible with the present invention. Accordingly, the closed-circuit respirator illustrated in FIG. 3 comprises patient-connector 114, ventilating conduits 118, 120 and variable volume reservoir 154.

In the instant exemplary embodiment, variable volume reservoir 154 is defined by rigid member 130 which is sealingly attached to compliant membrane 128. As the treated expiratory gas is forced into variable volume reservoir 154 increasing the pressure therein, compliant membrane 128 expands to increase the volume defined by rigid member 130 and compliant membrane 128. That is, the volume of variable volume reservoir 154 is increased to equalize the interior pressure and the exterior pressure. The interior pressure of variable volume reservoir may be regulated by biasing inspiratory check valve 126 in a closed position. The amount of bias will determine the allowed pressure differential between the pressure in the gas flow path defined by inspiratory ventilating conduit 118 and the pressure in variable volume reservoir 154. This bias may be regulated by simple mechanical resistance built into inspiratory check valve 126 or may be adjusted based on data received from sensor means. In any case, when the pressure differential exceeds the biasing force, such as when negative pressure is exerted on the gas flow path defined by inspiratory ventilating conduit 118, check valve 126 will open and ventilating gas will pass from variable volume reservoir 154, simultaneously reducing its volume, into ventilating conduit 118.

Those skilled in the art will appreciate that the illustrated configuration of variable volume reservoir is exemplary only and that numerous designs exhibiting the desired characteristics of expansion or contraction may be employed in the present invention. For example, the variable volume reservoir may be in the form of a balloon like structure, a bellows or a floating piston. Whatever form is selected, it is clearly within the scope of the present invention to manually or mechanically manipulate the variable volume reservoir so as to effect positive pressure ventilation. This technique is analogous to "bagging the patient" with conventional open-circuit ventilation devices and may be especially useful in emergency procedures. When used in this manner the closed-circuit system illustrated in FIG. 3 may be employed without any sensors or electro-mechanical equipment whatsoever. For example, oxygen may be slowly metered into the gas flow path defined by the closed-circuit respirator while respiration is effected spontaneously or by manipulating the variable volume reservoir. Such methods may be used to stabilize the patient and keep them alive until more sophisticated instrumentation is available. Of course the same techniques may be used in non-emergency situations.

For more controlled situations, such as in-home care, sensors and gas introduction devices are preferably used in conjunction with the closed-circuit ventilation system. In FIG. 3, inspiratory gas controlled 132 may be used to introduce oxygen and other gases to the inspiratory gas. Sensor assembly 134 preferably comprises an oxygen sensor and may additionally incorporate pressure, temperature, flow, vapor and gas sensors. As the ventilation gas passes through inspiratory ventilating conduit 118 data is obtained from sensor assembly 134 and fed into inspiratory gas controller 132, and optionally, nebulizer 144. Inspiratory gas controller 132 is connected to external gas sources, including oxygen, through gas transfer lines 136, 138 and 140 and will introduce them into the gas flow path based on data from sensor assembly 134 in combination with preprogrammed instructions. Preferably these gases are introduced into variable volume reservoir through gas introduction line 142 to minimize pressure fluctuations and ensure mixing. However, they may be introduced at any point in the gas flow path. Similarly, nebulizer 144 may be used to introduce liquid medium or respiratory agents to the gas flow path as described above. Optional nebulizer check flow valve 146 reduces the chances of undesired backflow during the expiration phase. Finally, the inspiratory gas, including any circulated respiratory agent or liquid medium passes through patient-connector 114 and is introduced into the pulmonary air passages where the cycle starts a new.

Figure 4:
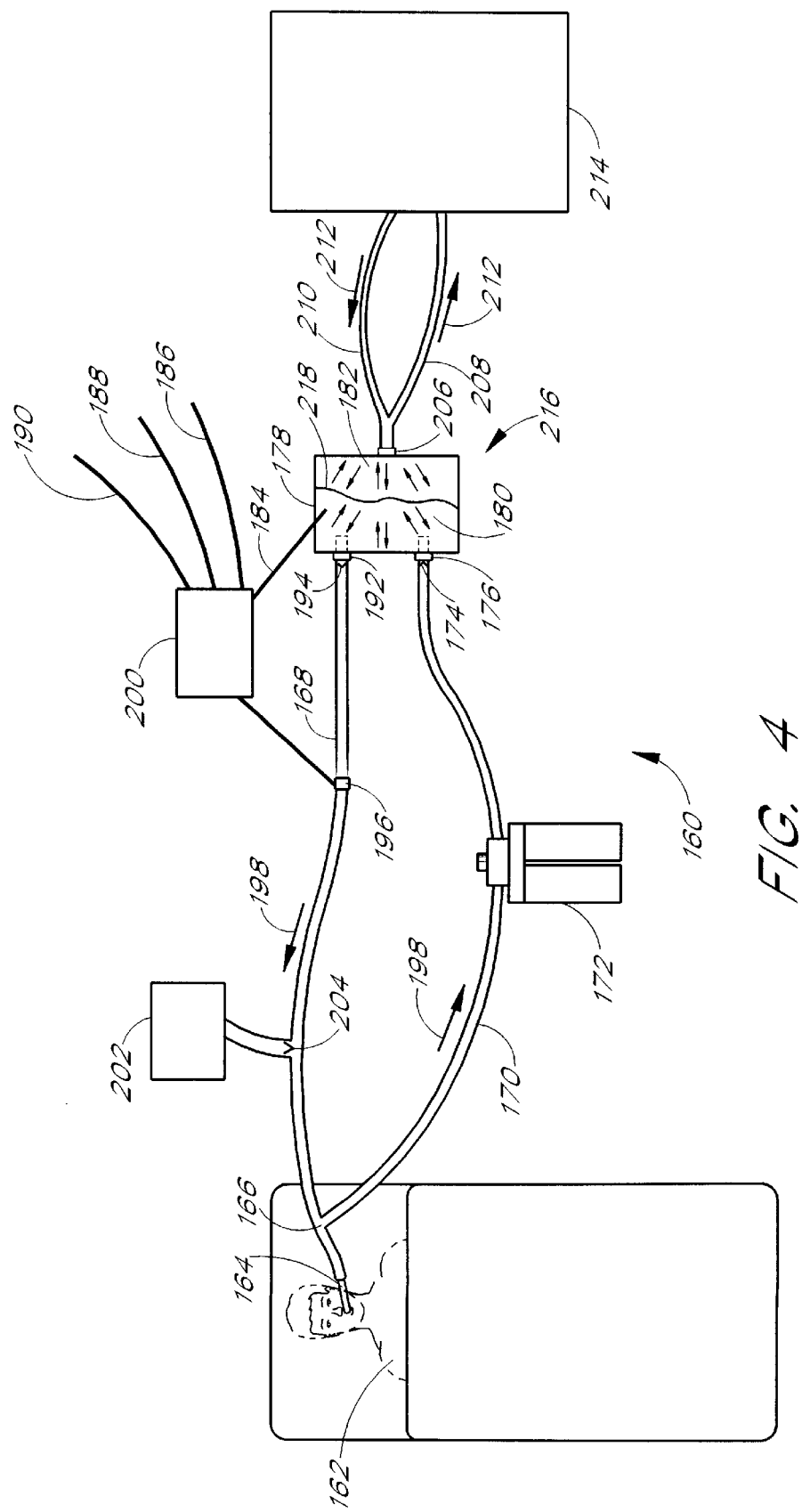
FIG. 4 is a schematic representation of an exemplary closed-circuit positive pressure ventilating system comprising a mechanical ventilator formed in accordance with the teachings herein.

FIG. 4 is a schematic representation of an embodiment of the present invention similar to that shown in FIG. 3 but capable of performing positive pressure ventilation. More particularly, the closed-circuit ventilation system depicted in FIG. 4 comprises a closed-circuit respirator defining a gas flow path that is operably associated with an unmodified open-circuit mechanical ventilator. By "operably associated" it is meant that gas flow and other ventilation may be controlled, monitored and effected by the connected ventilator apparatus. As with the previous embodiments of the present invention, the closed-circuit respirator allows the ventilating gas, treated to remove carbon dioxide, to be circulated in and out of the patient along with any incorporated vapor, gas or respiratory promoter. This closed-circuit ventilation provides all the previously discussed advantages such as retention of expensive materials, improved monitoring of ventilating gas components and containment of pathogenic agents. Yet, the embodiment shown in FIG. 4 provides the additional advantage of allowing closed-circuit pressure ventilation and particularly partial liquid ventilation, using off the shelf open-circuit mechanical ventilators with all their sophisticated respiratory controls. At the same time, isolation of the gas flow path from the ventilator apparatus allows modular adaptability, reduces materials compatibility problems, reduces regulatory complications and eliminates contamination problems from the repeated use of hard to sterilize ventilators. Moreover, as illustrated in FIG. 4, the present invention uniquely solves all of these problems in a simple, direct and cost efficient manner.

As indicated, closed-circuit ventilation system 160 depicted in FIG. 4 comprises many of the same elements as the embodiment shown in FIG. 3. As with the embodiment of FIG. 3, the closed-circuit respirator defining the gas flow path (represented by arrows 198) comprises patient-connector 164, ventilating conduits 168 and 170 and variable volume reservoir 180 wherein variable volume reservoir 180 is substantially analogous to variable volume reservoir 154 of FIG. 3 with the exception that the compliant membrane 218 devides the chamber 178 into two reservoirs that are not in fluid-conducting communication. Patient-connector 164, in this case an endotracheal tube, is positioned to establish fluid-conducting communication between the pulmonary air passages and expiratory ventilating conduit 170. During the spontaneous expiration phase, expiratory gas passes through the gas flow path defined by expiratory ventilating conduit 170 and through carbon dioxide separator 172 where it is treated as previously described. Upon exiting carbon dioxide separator 172, the treated gas advances through unidirectional check valve 174 and annular connector 176 where it exits the distal end of expiratory ventilating conduit 170 into variable volume reservoir 180 of isolation chamber 216.

As will be discussed in detail below, the ventilating gas (comprising treated expiratory gas incorporating introduced respiratory agents or) may be forced through annular connector 194 and unidirectional check valve 192 into inspiratory ventilating conduit 168. Prior to introduction into inspiratory ventilating conduit 168, the ventilating gas may be supplemented with oxygen and other gases introduced into variable volume reservoir 180 by inspiratory gas controller 200 from gas transfer lines 186, 188, 190 as previously described. The supplemented gas, preferably under positive pressure, then travels through inspiratory ventilating conduit 168, past sensor assembly 196 and into patient-connector 164. Like the embodiment of FIG. 3, sensor assembly 196 preferably transfers data to both inspiratory gas controller 200 and nebulizer 202. Nebulizer 202 may then interject vaporized respiratory agent or liquid medium to supplement the previously introduced recirculated material present in the inspiratory gas. The inspiratory gas containing the recirculated respiratory agent or liquid medium is then forced into the pulmonary air passages of patient 162 to effect positive pressure ventilation.

Unlike the embodiment depicted in FIG. 3, closed-circuit ventilation system 160 of FIG. 4 advantageously incorporates an unmodified open-circuit mechanical ventilator 214 in a modular configuration. More specifically, mechanical ventilator 214 is operably associated with the closed-circuit respirator defining the gas flow path. Mechanical ventilator 214 may be any commercially available ventilator and corresponds essentially to the open-circuit ventilation system depicted in FIG. 1 wherein ventilating gas is supplied from an external source and expiratory gas is vented into the surrounding environment. In the schematic representation of FIG. 4 the internal workings of the ventilator apparatus have been omitted for simplicity. Pressure conduit 210 and exhaust conduit 208 define a gas flow path (represented by arrows 212) which transmits pressurized gas from the mechanical ventilator 214 and vents exhaust gas. Those skilled in the art will appreciate that mechanical ventilator 214 comprises all the sophisticated control and delivery functions normally found on conventional mechanical ventilators, thereby allowing a wide range of gas administration modes to be selected.

In the preferred embodiment of the present invention shown in FIG. 4, mechanical ventilator 214 may be used to effect positive pressure ventilation on patient 162 by transmitting pressure waves through isolation chamber 216 and into the closed-circuit respirator as defined above. As depicted, isolation chamber 216 comprises chamber 178 which is bifurcated by compliant membrane 218 to define variable volume reservoir 180 and compression reservoir 182. The small arrows in chamber 178 are indicative of gas pressure on the various surfaces. Variable volume reservoir 180 and compression reservoir 182 are in direct pressure conducting communication through compliant membrane 218 but not in fluid-conducting communication. Preferably chamber 178 is constructed of a rigid or semi rigid material. Inspiratory ventilating conduit 168 and expiratory ventilating conduit 170 are sealingly affixed to chamber 178 thereby establishing fluid-conducting communication between the inspiratory gas flow path and variable volume reservoir 180 as well as the expiratory gas flow path and variable volume reservoir 180. FIG. 4 also shows that pressure conduit 210 and exhaust conduit 208 are sealingly attached to chamber 178 by annular connector 206 thereby establishing fluid-conducting communication between mechanical ventilator 214 and compression reservoir 182. Those skilled in the art will appreciate that the configuration depicted is exemplary only and that other configurations may work equally well. For example, chamber 178 may be spherical or variable volume reservoir 180 and compression reservoir 182 may be oriented differently.

In any case, isolation chamber 216 may be used to pressurize, in a controlled manner, the gas flow path defined by the closed-circuit respirator. As discussed above, the treated expiratory gas is forced through the gas flow path defined by expiratory ventilating conduit 170 and into variable volume reservoir 180 by spontaneous exhalation. Unidirectional expiratory check valve 174 prevents undesirable backflow. Introduction of the treated expiratory gas increases pressure in variable volume reservoir 180. Compliant membrane 218 adjusts to this pressure fluctuation by moving to increase the volume of variable volume reservoir and normalize pressure between variable volume reservoir 180 and compression reservoir 182.

At the same time, mechanical ventilator 214 is delivering gas under positive pressure through pressure conduit 210 to compression reservoir 182. It will be appreciated that the gas may be delivered employing any one of the numerous sophisticated delivery profiles available with modern ventilators. Preferably the delivery profile will be coordinated with the respiration efforts of patient 162. As the gas is introduced under pressure to compression reservoir 182, compliant membrane 218 reacts to increase the volume of compression reservoir 182 while simultaneously reducing the volume of variable volume reservoir 180 and pressurizing the gas flow path defined by the closed-circuit respirator. This increased pressure forces ventilating gas through inspiratory ventilating conduit 168 to effect positive pressure ventilation of patient 162. In other words, the pressure fluctuations generated by mechanical ventilator 214 are transferred to the gas flow path through isolation chamber 216. Advantageously, the delivery profile produced by mechanical ventilator 214 is conserved as it is transmitted though isolation chamber 216. Accordingly, delivery profiles may be selected which maximize compliance and minimize resistance.

As indicated above, the unique modular construction of the closed-circuit ventilation systems of the present invention allows different ventilation components to be substituted or interchanged depending on the specific needs of the physician. For example, in the embodiment depicted in FIG. 4 any commercially available mechanical ventilator may be operably associated with the selected closed-circuit respirator rapidly and easily. Similarly, optional equipment such as sensors and vaporizers may be quickly changed to modify the configuration of the ventilation system based on therapeutic needs. This modularity allows the closed-circuit systems of the present invention to be rapidly changed periodically, for example to avoid bacterial growth, without unduly interrupting the therapeutic procedure. In this case the closed-circuit respirator could be rapidly disconnected from the patient and any associated ventilator and replaced with a fresh sterile one which had been prepackaged. Further, in accordance with the teachings herein, the used closed-circuit respirator could be sterilized and reused or discarded. The modular construction of the present invention also facilitates maintenance and system cleaning.

As previously indicated the present invention provides for the independent delivery of pharmaceutical agents or their use in conjunction with other vapors or gases such as respiratory promoters. Moreover, the devices and methods of the present invention may be used for the therapeutic administration of pharmaceutical agents in conjunction with any type of ventilation. In particular, combining pharmaceutical dosing regimens with liquid ventilation therapy has a number of advantages over other forms of drug delivery. The fluorochemical-enhanced delivery can be used for medicaments that would otherwise be ineffective or destroyed by delivery systemically. For example, proteins usually cannot be administered orally because they are destroyed in the alimentary tract. Some proteins may invoke severe allergic reactions and shock in the host if administered systemically such as intramuscularly or intravenously.

For example, antibiotics and antivirals may be provided in combination with a fluorochemical liquid during either partial liquid ventilation or total liquid ventilation. One particular pathogenic agent, cytomegalovirus can induce life-threatening cases of pneumonia in immunocompromised patients. These individuals often require ventilation therapy. Fluorocarbon administration in combination with the guanosine nucleoside analog, 9-(1,3-dihydroxy-2-propoxymethyl)guanine, otherwise known as Ganciclovir or DHPG, may provide an effective therapy that could simultaneously inhibit viral replication and facilitate oxygen transport in the compromised lung.

The precise amount of pharmaceutical agent administered in conjunction with the methods and devices of the present invention is dependent upon the agent of choice, the required dose, and the form of the drug actually introduced. Those skilled in the art will appreciate that such determinations may be made by using well-known techniques in combination with the teachings of the present invention.

Preferred pharmaceutical agents comprise respiratory agents, antibiotics, antivirals, mydriatics, antiglaucomas, anti-inflammatories, antihistaminics, antineoplastics, anesthetics, ophthalmic agents, cardiovascular agents, active principles, nucleic acids, genetic material, immunoactive agents, imaging agents, immunosuppressive agents, gastrointestinal agents and combinations thereof. Further exemplary embodiments of the present invention comprise anti-inflammatory agents such as the glucocorticosteroids (i.e. cortisone, prednisone, prednisolone, dexamethasone, betamethasone, Beclomethasone diproprionate, Triamcinolone acetonide, Flunisolide), xanthines (i.e. theophylline, caffeine), chemotherapeutics (i.e. cyclyphosphamide, lomustine, methotrexate, cisplatin, taxane derivatives), antibiotics (i.e. aminoglycosides, penicillins, cephalosporins, macolides, quinolones, tetracyclines, chloramphenicol, bronchodilators such as the $B_2$-agonists (i.e. adrenaline, isoprenaline, salmeterol, albuterol, salbutamol, terbutaline, formoterol) and surfactants. Still other exemplary embodiments include a/β adrenergic blockers (i.e. NormodyneÔ, TrandateÔ), angiotensin converting enzyme inhibitors (i.e. VasotecÔ), antiarrhythmics, beta blockers, calcium channel blockers, inotropic agents, vasodilators, vasopressors, anesthetics (i.e. morphine) and ophthalmic agents (i.e. Polymyxin B, Neomycin, Gramicidin).

In addition to enhanced drug delivery, liquid mediums such as fluorochemicals can be used to remove endogenous or foreign material from the interior of the lungs during closed-circuit ventilation therapy. Fluorochemical liquid can be substituted for conventional physiological saline solutions used in lavage and may be introduced as described herein. Because fluorochemicals are oxygenatable, they provide oxygen to the person during the treatment allowing for longer and less dangerous lavage procedure. In addition, because some fluorochemicals have lung surfactant properties, removal of the natural lung surfactant is minimized. The density of fluorochemical liquids is generally twice that of water and body tissue which permits the fluorochemical to sink below and displace the material to be removed. Then when the fluorochemical is removed by mechanical means well known in the practice of lavage, the displaced material will float and be simultaneously removed. These properties are particularly important when lavage is combined with liquid ventilation-enhanced drug delivery as a complete treatment of, for example, a patient with cystic fibrosis whose lungs accumulate excess mucinous secretions.

As discussed above, effective respiratory therapy and pulmonary delivery of pharmaceutical agents may also be achieved using total liquid ventilation. In TLV both the lungs and the ventilation system are substantially filled with oxygenatable liquid respiratory promoter which is then circulated in and out of the pulmonary air passages to effect respiration. As a liquid respiratory promoter is employed rather than a gas or vapor saturated gaseous medium, conventional mechanical ventilators may not be used in the procedure. Further, when performing TLV using dedicated liquid ventilation equipment, substantial amounts of the liquid respiratory promoter are lost into the surrounding environment due to the techniques used to remove the carbon dioxide exhaled by the patient. Unfortunately, the loss of the potentially expensive liquid respiratory promoter renders a relatively promising therapeutic procedure much less attractive in today's fiscal environment.

Figure 5:
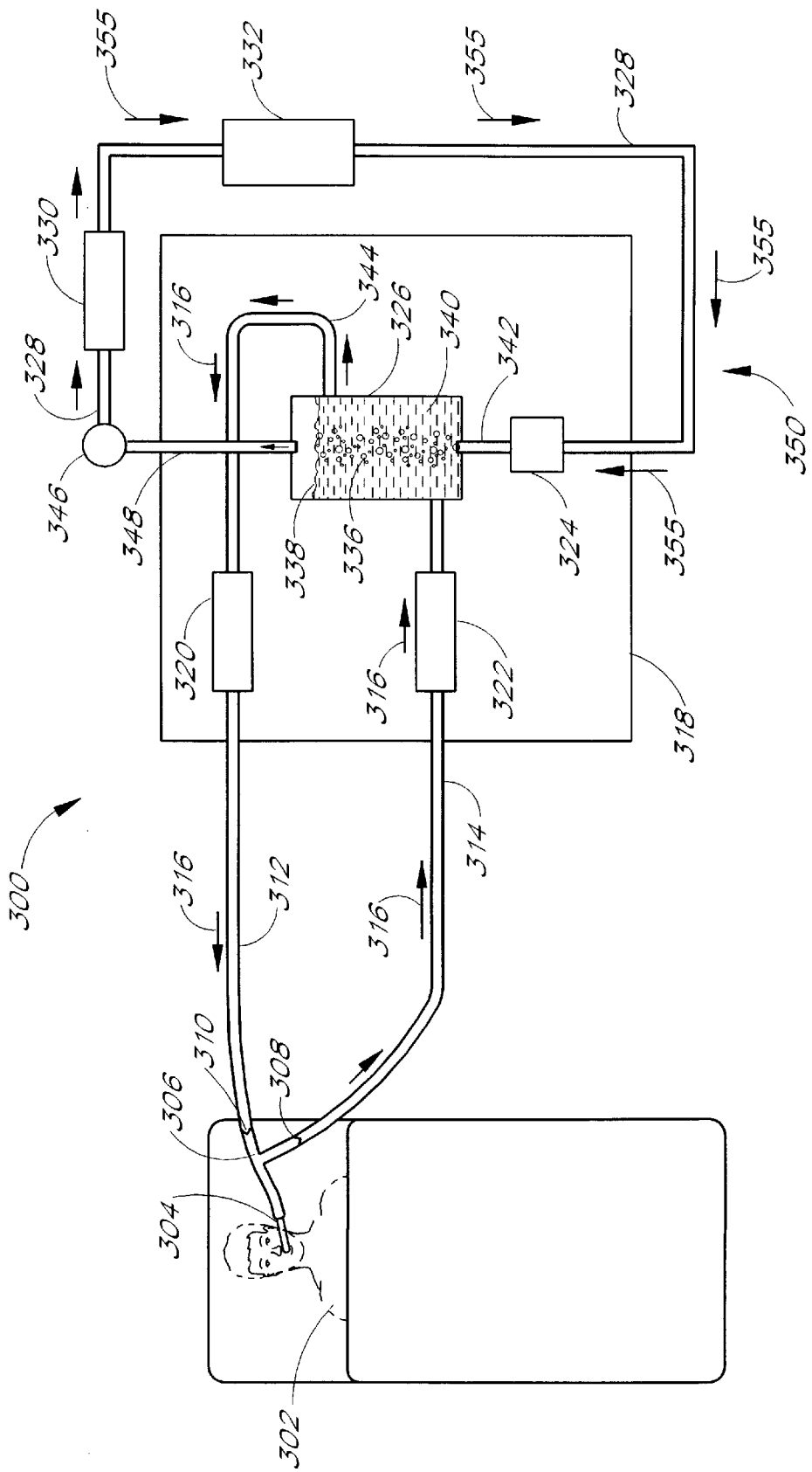
FIG. 5 is a schematic representation of a closed-circuit total liquid ventilation system having a closed-circuit vapor separator positioned exogenously with respect to the closed-circuit respirator.
Figure 6:
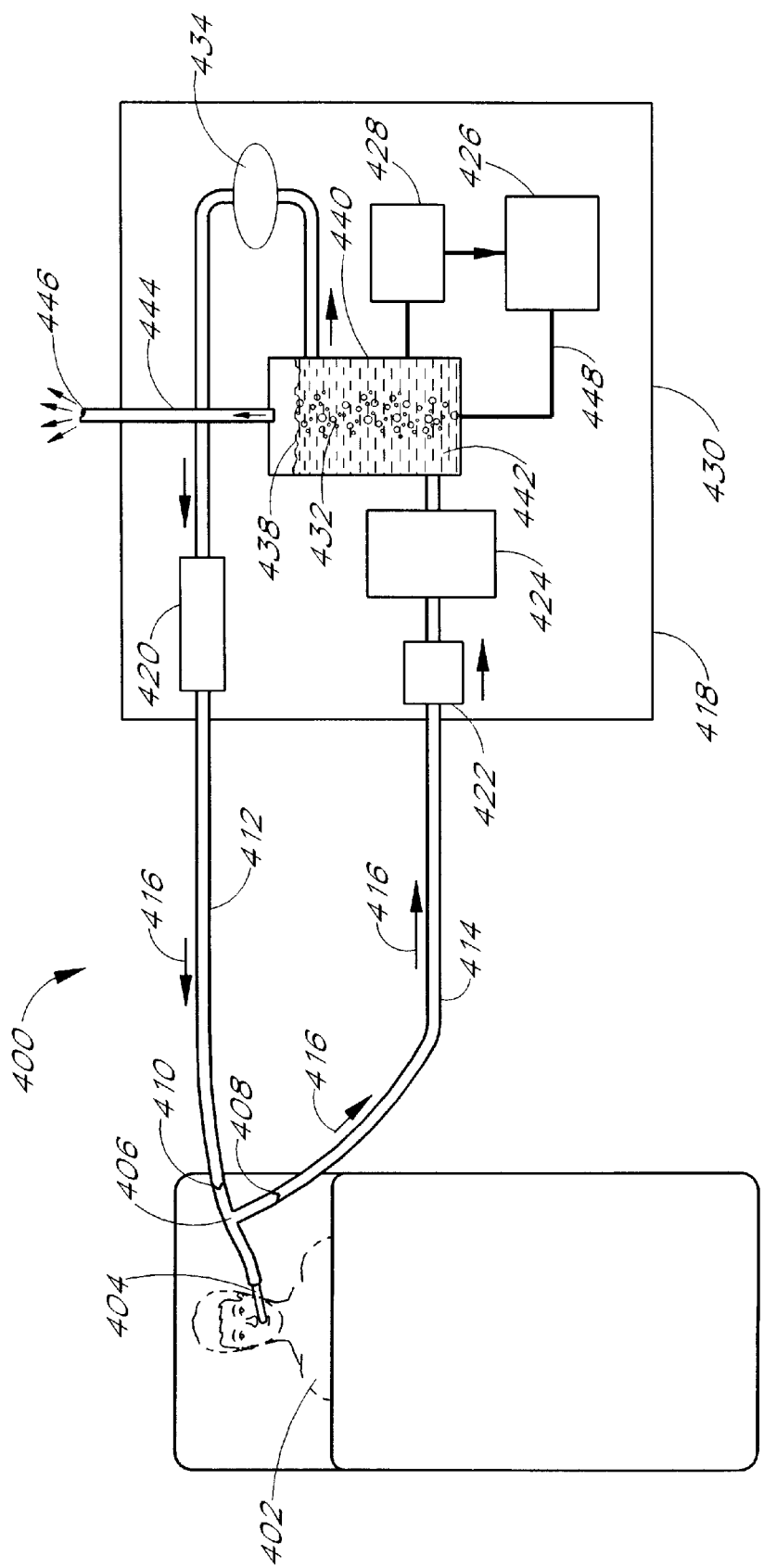
FIG. 6 is a schematic representation of an exemplary closed-circuit total liquid ventilation system having a liquid scrubber in-line with the closed-circuit respirator.

The methods and apparatus of the present invention, as shown by the embodiments in FIGS. 5 and 6, largely obviate this problem and substantially increase the cost-effectiveness of the therapy while, at the same time, enhance its efficacy. FIG. 5 is a schematic representation of closed-circuit TLV system 300 attached to patient 302. As may be seen by examination of the figure, closed-circuit TLV system 300 actually achieves the objectives of the present invention by combining two substantially closed-circuit arrangements to provide total liquid ventilation with the efficient retention of the circulating liquid respiratory promoter. Specifically, the illustrated embodiment of the present invention combines a closed-circuit liquid respirator, operably associated with a liquid ventilator, with a closed-circuit gaseous carbon dioxide removal system to provide a unique apparatus for TLV therapy. By operably associated it is meant that fluid flow and ventilation procedures are controlled and monitored by the liquid ventilator. In short, the carbon dioxide from the lungs is disassociated from the circulating liquid respiratory promoter through the introduction of gaseous oxygen, preferably in a gas exchange unit. The disassociated carbon dioxide, now in a gaseous form, is then separated from closed-circuit TLV system 300 as it circulates through the second closed-circuit system comprising a vapor separator before the treated gas is returned to the circulating liquid respiratory promoter.

More particularly, in FIG. 5 closed-circuit TLV system 300 is in fluid-conducting communication via patient-connector 304 which in this embodiment is an endotracheal tube. During the inspiration phase of the respiration cycle, oxygen rich liquid respiratory promoter is introduced into the pulmonary air passages under positive pressure. During exhalation, a portion of this liquid respiratory promoter comprising pulmonary waste products including carbon dioxide is forced from the lungs either by spontaneous expiration or under negative pressure supplied by the closed-circuit liquid respirator. The carbon dioxide associated with the liquid respiratory promoter may be, but is not necessarily, dissolved. In any case this expiratory liquid passes through patient-connector 304, past Y-connector 306 and, as with the previously described embodiments, into the fluid flow path defined by expiratory ventilating conduit 314. In accordance with the other embodiments, expiratory unidirectional check valve 308 and inspiratory unidirectional check valve 310 ensure that the expiratory fluid only enters expiratory ventilating conduit 314. Arrows 316 depict the fluid flow path defined by the closed-circuit liquid respirator of the instant embodiment. The expiratory fluid passes through expiratory ventilating conduit 314 and enters liquid ventilating apparatus 318 driven by optional expiratory fluid pump 322 in fluid-conducting communication with the fluid flow path. Those skilled in the art will appreciate that liquid ventilator 318 performs many of the same functions regarding monitoring and control of the procedure as do the mechanical ventilation devices previously described. In particular liquid ventilator 318 comprises a number of sensors (not shown) that provide real time data on system parameters such as medium temperature, composition, flow rate, pressure, oxygen levels, carbon dioxide levels, etc. Further, based on the information received and preprogrammed instructions liquid ventilator 318 controls the flow rate, pulmonary delivery profile and pressure of the circulating liquid respiratory promoter through fluid pumps 318 and 322 and a series of flow control valves (not shown). With such controls, liquid ventilator 318 may provide delivery profiles and specific medium compositions as complex as those produced by traditional gas ventilators.

Optional expiratory fluid pump 322 propels the expiratory fluid comprising carbon dioxide into gas exchanger 326 from the distal end of expiratory ventilating conduit 314. Those skilled in the art will appreciate that gas exchanger 326 is not limited to any one configuration or method of operation but rather may be any apparatus that allows the disassociation of carbon dioxide from the expiratory fluid. In the embodiment shown, gas exchanger 326 comprises fluid reservoir 340 wherein oxygen and other gases are bubbled through collected liquid respiratory promoter comprising associated carbon dioxide. Here, as will be discussed in detail later, gaseous oxygen is introduced into gas exchanger 326 from vapor inlet conduit 342 which is in fluid-conducting communication with fluid reservoir 340. As is known in the art, the introduction of oxygen into liquid respiratory promoter comprising associated carbon dioxide will force the disassociation of carbon dioxide from the medium and drive it into the gas phase. As the same time the oxygen associates with the liquid respiratory promoter, preferably in a dissolved state. Of course, as with other disassociated gases, the carbon dioxide will bubble to the surface of the circulating liquid respiratory promoter. For the purposes of the present invention enough gaseous oxygen is introduced to fluid reservoir 340 to disassociate at least a portion of the carbon dioxide contained in the liquid respiratory promoter. Bubbles 336 represent the gaseous oxygen and resulting disassociated carbon dioxide passing through the liquid respiratory promoter to fluid surface 338. Suitable sensors (not shown) will be normally be provided to monitor the gas composition of the liquid respiratory promoter and provide real time data for control of the system.

Following disassociation of the carbon dioxide, the oxygenated liquid respiratory promoter passes through the fluid flow path defined by inlet ventilating conduit 344 and is propelled into inspiratory ventilating conduit 312, preferably by inspiratory fluid pump 320. In the embodiment shown, inlet ventilating conduit is maintained in fluid-conducting communication with fluid reservoir 340 below fluid surface 338 in order to prevent the unintentional introduction of free gas into the fluid flow path. Inspiratory fluid pump 320 forces the oxygenated liquid respiratory promoter, comprising material which had previously been introduced into the lungs, through the fluid flow path defined by inspiratory ventilating conduit 312, Y-connector 306 and patient-connector 304, passing unidirectional inspiratory check valve 306 prior to entry into the pulmonary air passages. That is, liquid respiratory promoter is circulated through the gas flow path defined by patient-connector 304, expiratory ventilating conduit 314, gas exchanger 336, inlet ventilating conduit 344 and inspiratory ventilating conduit 316 to be reintroduced into the pulmonary air passages thereby effecting total liquid ventilation. The liquid respiratory promoter may be recirculated in and out of the lung indefinitely in this manner.

As previously discussed, oxygen is bubbled through fluid reservoir 340, preferably under pressure, to disassociate carbon dioxide from the liquid medium previously used for respiration. Following the disassociation of the carbon dioxide from the circulating liquid respiratory promoter and its passage through fluid surface 338. Typically, not all of the introduced oxygen is associated with the treated liquid respiratory promoter leaving some to travel through gas exchanger 326 and pass through fluid surface 338. Moreover, a substantial amount of the liquid respiratory promoter is forced into a vaporous state above fluid surface 338 due to system thermodynamics. In conventional open-circuit TLV systems, this vaporous mixture comprising oxygen, carbon dioxide and vaporized liquid medium would be vented into the surrounding medium and lost. Conversely, in the embodiment of the present invention illustrated in FIG. 5 this vaporous mixture enters closed-circuit vapor separator 350 defining a vapor flow path. Vapor movement through the vapor flow path is represented by arrows 355. Passing through this vapor flow path, the carbon dioxide is chemically bound and removed from a gaseous state while the treated vapor comprising liquid respiratory promoter and oxygen is circulated and reintroduced to fluid reservoir 340 thereby minimizing the loss of liquid respiratory promoter during ventilation therapy.

More particularly, the vapor is forced into the vapor flow path defined by vapor inlet conduit 348 via positive pressure from gas exchanger 326. From here the vapor passes through optional gas pressure controller 346 and into vapor transfer conduit 328. Gas pressure controller may be used to regulate the pressure and flow of the vapor thereby maintaining thermodynamic equilibrium and a constant fluid level in fluid reservoir 340 and this may vent excess gas pressure from the system as required to maintain near ambient pressure. The vapor passes along the vapor flow path propelled by vapor moving apparatus 330 which is in fluid-conducting communication with vapor transfer conduit 328. Those skilled in the art will appreciate that vapor moving apparatus 330 may be positioned anywhere along the vapor flow path and may comprise a blower or a pump. The vapor then passes into carbon dioxide separator 332, in fluid-conducting communication with the vapor flow path, where at least a portion of the carbon dioxide is removed from the gas phase and deposited on the surface of a solid as previously discussed. From here the treated vapor passes through the vapor flow path defined by vapor transfer conduit 328 and vapor inlet conduit 342 before being reintroduced into liquid reservoir 340. Optional controller 324 may be used to introduce oxygen or other gases to the vapor flow path or directly to gas exchanger. Preferably controller 324 is receiving data from liquid ventilator 318 or from independent sensors regarding flow rate, vapor composition, oxygenation levels, etc. Of course those skilled in the art will appreciate that oxygen and other gases may be introduced at any point along the fluid flow path or the vapor flow path.

Another embodiment of the present invention that may be used for closed-circuit TLV therapy is schematically depicted in FIG. 6. As with the previous embodiment, the instant figure illustrates a closed-circuit TLV system comprising a closed-circuit respirator operably associated with a liquid ventilator. However, unlike the embodiment detailed in FIG. 5, FIG. 6 shows a closed-circuit TLV system comprising a liquid scrubber rather than a closed-circuit vapor separator. This liquid scrubber is in fluid-conducting communication with the closed-circuit respirator and separates carbon dioxide directly from the circulating respiratory promoter rather tan from a gaseous vapor. Following removal of at least a portion of the carbon dioxide, the liquid respiratory promoter is oxygenated and circulated through the remainder of the system to be reintroduced to the lungs of the patient.

Specifically, closed-circuit TLV system 400 is connected to patient 402 via patient-connector 404 establishing fluid-conducting communication between the pulmonary air passages and the fluid flow path (illustrated by arrows 416) defined by the closed-circuit respirator. Patient 402 is undergoing total liquid ventilation as previously described. Upon expiration, the expiratory fluid from the pulmonary air passages is forced through patient-connector 404, past unidirectional inspiratory check valve 408 and into inspiratory ventilating conduit 414. Optional fluid pump 422 propels the expiratory fluid into liquid ventilator 418 and into liquid scrubber 424 which is in fluid-conducting communication with the fluid flow path defined by the closed-circuit liquid respirator. As described above, preferably the closed-circuit liquid respirator is operably associated with liquid ventilator 418 which monitors and controls the parameters of the therapeutic procedure.

Liquid scrubber 424 is preferably a modular unit comprising a liquid impermeable shell containing a material capable of binding carbon dioxide and separating it from the circulating respiratory promoter. As with the carbon dioxide separators alluded to earlier, liquid scrubber 424 may comprise a base material which reacts with the carbon dioxide in the circulating liquid respiratory promoter to form a carbonate that is deposited on the surface of the material and water. Exemplary materials that are suitable for use as liquid scrubbers in the present invention comprise, but are not limited to, lithium hydride and soda lime. Preferably, the modular units will be easy to change or recharge without substantially interfering with ongoing therapy. Moreover, in preferred embodiments the fluid flow exiting from liquid scrubber 424 will be monitored using sensors associated with liquid ventilator 418 to provide real time data as to the amount of carbon dioxide being separated.

Following separation of at least a portion of the carbon dioxide associated with the expiratory fluid, the treated liquid respiratory promoter is propelled through the remainder of expiratory ventilating conduit 414 and into gas exchanger 440. In the illustrated embodiment, gas exchanger 440 comprises fluid reservoir 442 which is filled with liquid respiratory promoter having a fluid surface 338. Gaseous bubbles 432, generated by gas injector 426 and introduced from gas inlet line 448, are rising through the liquid respiratory promoter which is preferably being agitated or stirred. Preferably, gas release rates and composition are regulated by gas controller 428 which is receiving physical parameters associated with gas exchanger 440 and from liquid ventilator 430. Among other gases, oxygen may be introduced to gas exchanger 440 to oxygenate the liquid respiratory promoter therein. Those skilled in the art will appreciate that oxygen may be introduced anywhere along the fluid flow path to provide oxygenated liquid respiratory promoter and that the configuration and inclusion of gas exchanger 440 is exemplary only.

Unlike the embodiment depicted in FIG. 5 where substantial amounts of oxygen was introduced to disassociate carbon dioxide from the liquid respiratory promoter, the oxygen introduced in the instant embodiment is merely to replace the oxygen used by patient 402 during respiration. Accordingly, relatively small amounts of oxygen need be introduced into the circulating liquid respiratory promoter to provide the desired oxygen content. Moreover, the gas introduction may be done very gently allowing most of the introduced oxygen to dissolve in the liquid and leaving very little to actually bubble through fluid surface 438. The gentle introduction and low amounts of oxygen introduced mean that very little liquid respiratory promoter is vaporized above fluid surface 438. Further, due to the slow introduction of oxygen and its dissolution in the circulating liquid respiratory promoter, pressure buildup in gas exchanger 440 is relatively low. However, optional gas outlet conduit 444, in fluid-conducting communication with fluid reservoir 442, may be provided for the venting of gases to maintain a stable equilibrium in gas exchanger 440. Small amounts of gaseous oxygen comprising low levels of respiratory promoter may be released through vent 446 in this manner. Pressure regulators or valves (not shown) on optional gas outlet conduit 444 may be used to further reduce the amount of liquid respiratory promoter lost.

Following oxygenation, the oxygenated liquid respiratory promoter is transported to patient 402 and reintroduced into the pulmonary air passages substantially as described above. In particular, the liquid respiratory promoter is forced into inspiratory ventilating conduit 412, transported through optional inspiratory reservoir 434 and passes through inspiratory fluid pump 420. From here the oxygenated respiratory promoter passes along the fluid flow path defined by inspiratory ventilating conduit 412, past unidirectional inspiratory check valve 410 and Y-connector 406, through patient-connector 404 and into the pulmonary air passages whereby total liquid ventilation is effected.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the invention.

What is claimed is:

1. A process for closed-circuit partial liquid ventilation therapy comprising the steps of:

introducing at least one non-anesthetic gas or vapor into pulmonary air passages of a respiring patient;

capturing expiratory gas from said patient in a closed-circuit respirator in fluid-conducting communication with said pulmonary air passages, said expiratory gas comprising carbon dioxide and at least a portion of said introduced gas or vapor;

circulating said expiratory gas through a gas flow path defined by said closed-circuit respirator wherein at least a portion of said carbon dioxide is removed; and thereafter reintroducing at least a portion of the circulated expiratory gas comprising said introduced gas or vapor into the pulmonary air passages of the patient.

2. The process of claim 1 wherein said non-anesthetic gas or vapor comprises the gaseous phase of a fluid present in the pulmonary air passages.

3. The process of claim 1 wherein said gas or vapor is a bioactive agent.

4. The process of claim 1 wherein said gas or vapor is a respiratory promoter.

5. The process of claim 4 wherein said respiratory promoter is a fluorochemical.

6. The process of claim 5 wherein said fluorochemical respiratory promoter selected from the group consisting of FC-75, FC-77, RM-101, Hostinert 130, APF-145, APF-140, APF-125, perfluorodecalin, perfluorooctyl bromide, perfluorobutyltetrahydrofuran, perfluoropropyl-tetrahydropyran, dimethyladamantane, trimethyl-bicyclo-nonane, and mixtures thereof.

7. The process of claim 5 wherein said fluorochemical respiratory promoter is perfluorooctyl bromide.

8. The process of claim 5 wherein said fluorochemical is a liquid at body temperature.

9. The process of claim 1 further comprising the step of pressurizing at least a portion of said gas flow path to effect positive pressure ventilation of said patient.

10. The process of claim 7 further comprising the step of effecting positive pressure ventilation of the patient by applying pressure to said gas flow path from a mechanical ventilator operably associated with said closed-circuit respirator.

11. The process of claim 10 wherein said respiratory promoter is perfluorooctyl bromide.

12. The process of claim 1 further comprising the step of:

providing said closed-circuit respirator by affixing a ventilating conduit to a patient-connector capable of establishing fluid-conducting communication with pulmonary air passages of a patient and a variable volume reservoir, wherein said patient-connector is placed in fluid-conducting communication with said variable volume reservoir.

13. The process of claim 12 wherein said variable volume reservoir comprises a chamber bifurcated by a gas impermeable compliant membrane wherein said chamber is separated into said variable volume reservoir and a compression reservoir isolated from each other;

establishing fluid-conducting communication between said pulmonary air passages and said variable volume reservoir; and operably associating a mechanical ventilator with said closed-circuit respirator by establishing fluid-conducing communication between said mechanical ventilator and said compression reservoir.

14. The process of claim 13 further comprising the step of effecting positive pressure ventilation of the patient by using said mechanical ventilator to generate pressure waves to actuate said gas impermeable membrane whereby pressure is exerted on said gas flow path.

15. The process of claim 12 further comprising the step of pressurizing said variable volume reservoir to effect positive pressure ventilation of said patient.

16. The process of claim 15 further comprising the step of effecting positive pressure ventilation of the patient by applying pressure to said variable volume reservoir using a mechanical ventilator operably associated with said closed-circuit respirator.

17. A modular apparatus for closed-circuit partial liquid ventilation therapy whereby at least a portion of gas or vapor exhaled by a patient attached thereto is treated to remove carbon dioxide and returned to the patient, said apparatus comprising:

a patient-connector capable of establishing fluid-conducting communication with pulmonary air passages of a patient;

a variable volume reservoir containing a gas or vapor;

a ventilating conduit sealingly affixed to said patient-connector and said variable volume reservoir wherein said patient-connector is placed in fluid-conducting communication with said variable volume reservoir to provide a closed-circuit respirator defining a gas flow path; and a carbon dioxide separator in fluid-conducting communication with said gas flow path.

18. The apparatus of claim 17 wherein said ventilating conduit comprises an expiratory ventilating conduit defining an expiratory gas flow path and an inspiratory ventilating conduit defining an inspiratory gas flow path, said inspiratory and expiratory ventilating conduits having a proximal end and a distal end.

19. The apparatus of claim 18 wherein the proximal ends of said inspiratory ventilating conduit said and expiratory ventilating conduit are sealingly attached to said patient-connector and the distal ends of said inspiratory and expiratory ventilating conduits are sealingly attached to said variable volume reservoir.

20. The apparatus of claim 18 further comprising a respiratory promoter contained in said gas flow path.

21. The apparatus of claim 20 wherein said respiratory promoter is a fluorochemical.

22. The apparatus of claim 21 wherein said fluorochemical respiratory promoter is perfluorooctyl bromide.

23. The apparatus of claim 21 wherein said fluorochemical respiratory promoter selected from the group consisting of FC-75, FC-77, RM-101, Hostinert 130, APF-145, APF-140, APF-125, perfluorodecalin, perfluorooctyl bromide, perfluorobutyltetrahydrofuran, perfluoropropyl-tetrahydropyran, dimethyladamantane, trimethyl-bicyclo-nonane and mixtures thereof.

24. The apparatus of claim 20 wherein said respiratory promoter is selected from the group consisting of gases, liquids and vapors.

25. The apparatus of claim 20 wherein said respiratory promoter is a liquid breathing agent.

26. The apparatus of claim 17 wherein said variable volume reservoir comprises a chamber bifurcated by a gas impermeable compliant membrane, said compliant membrane separating said chamber into a compression reservoir and said variable volume reservoir isolated from one another, said variable reservoir in fluid-conducting communication with said ventilating conduit.

27. The apparatus of claim 26 further comprising a mechanical ventilator capable of providing positive pressure ventilation, said mechanical ventilator operably associated with said compression reservoir of said chamber whereby operation of the ventilator will transmit a pressure wave through said compliant membrane into said variable volume reservoir.

28. The apparatus of claim 27 further comprising a respiratory promoter contained in said gas flow path.

29. The apparatus of claim 28 wherein said respiratory promoter is perfluorooctyl bromide.

30. The apparatus of claim 17 further comprising a nebulizer in fluid-conducting communication with said gas flow path.

31. The apparatus of claim 17 further comprising a gas injector in fluid-conducting communication with said gas flow path.

32. A modular apparatus for closed-circuit partial liquid ventilation therapy comprising:
a patient-connector capable of establishing fluid-conducting communication with pulmonary air passages of a patient;
a ventilating conduit sealingly affixed to said patient-connector to provide a closed-circuit respirator defining a gas flow path, said closed-circuit respirator operably associated with a mechanical ventilator; and
a carbon dioxide separator in fluid-conducting communication with said gas flow path.

33. The apparatus of claim 32 wherein said ventilating conduit comprises an expiratory ventilating conduit defining an expiratory gas flow path, an inspiratory ventilating conduit defining an inspiratory gas flow path and a recovery ventilating conduit having a first end and a second end defining a recovery gas flow path, said inspiratory and expiratory ventilating conduits having a proximal end and a distal end.

34. The apparatus of claim 33 wherein the proximal ends of said inspiratory ventilating conduit and said expiratory ventilating conduit are sealingly attached to said patient-connector and the distal ends of said inspiratory and expiratory ventilating conduits are sealingly attached to said first and second ends of said recovery ventilating conduit respectively, wherein fluid-conducting communication is established between said distal end of said inspiratory ventilating conduit and said distal end of expiratory ventilating conduit.

35. The apparatus of claim 34 further comprising a variable volume reservoir in fluid-conducting communication with said closed-circuit respirator.

36. The apparatus of claim 34 further comprising a gas moving apparatus in fluid-conducting communication with said closed-circuit respirator.

37. The apparatus of claim 32 further comprising a respiratory promoter contained in said gas flow path.

38. The apparatus of claim 37 wherein said respiratory promoter is selected from the group consisting of gases, liquids and vapors.

39. The apparatus of claim 37 wherein said respiratory promoter is a liquid breathing agent.

40. The apparatus of claim 37 wherein said respiratory promoter is a fluorochemical.

41. The apparatus of claim 40 wherein said fluorochemical respiratory promoter selected from the group consisting of FC-75, FC-77, RM-101, Hostinert 130, APF-145, APF-140, APF-125, perfluorodecalin, perfluorooctyl bromide, perfluorobutyltetrahydrofuran, perfluoropropyltetrahydropyran, dimethyladamantane, trimethyl-bicyclononane and mixtures thereof.

42. The apparatus of claim 40 wherein said fluorochemical respiratory promoter is perfluorooctyl bromide.

43. The apparatus of claim 32 further comprising a nebulizer in fluid-conducting communication with said gas flow path.

44. The apparatus of claim 32 further comprising a gas injector in fluid-conducting communication with said gas flow path.

45. A process for closed-circuit partial liquid ventilation comprising:
connecting an exogenous closed-circuit respirator defining a gas flow path to the pulmonary air passages of a respiring patient;
introducing a respiratory promoter into said pulmonary air passages;
capturing expiratory gas from said patient in said closed-circuit respirator, said expiratory gas comprising carbon dioxide and at least a portion of said introduced respiratory promoter;
separating at least a portion of said carbon dioxide to provide a treated gas comprising said respiratory promoter; and
reintroducing said treated gas into the pulmonary air passages of the patient.

46. The process of claim 45 further comprising the step of administering a respiratory promoter to said pulmonary air passages of said respiring patient prior to said connecting step.

47. The process of claim 45 wherein said respiratory promoter is a liquid breathing agent.

48. The process of claim 45 wherein said respiratory promoter is a fluorochemical.

49. The process of claim 48 wherein said fluorochemical is a liquid at body temperature.

50. The process of claim 48 wherein said fluorochemical respiratory promoter selected from the group consisting of FC-75, FC-77, RM-101, Hostinert 130, APF-145, APF-140, APF-125, perfluorodecalin, perfluorooctyl bromide, perfluorobutyltetrahydrofuran, perfluoropropyltetrahydropyran, dimethyladamantane, trimethyl-bicyclononane, and mixtures thereof.

51. The process of claim 48 wherein said fluorochemical respiratory promoter is perfluorooctyl bromide.

52. The process of claim 45 further comprising the step of pressurizing at least a portion of said gas flow path to effect positive pressure ventilation of said patient.

53. The process of claim 52 further comprising the step of effecting positive pressure ventilation of the patient by applying pressure to said gas flow path from a mechanical ventilator operably associated with said closed-circuit respirator.

54. The process of claim 53 wherein said respiratory promoter is perfluorooctyl bromide.

55. The process of claim 45 further comprising the step of:
providing said closed-circuit respirator by affixing a ventilating conduit to a patient-connector capable of establishing fluid-conducting communication with pulmonary air passages of a patient and a variable volume reservoir, wherein said patient-connector is placed in fluid-conducting communication with said variable volume reservoir.

56. The process of claim 55 wherein said variable volume reservoir comprises a chamber bifurcated by a gas impermeable compliant membrane wherein said chamber is separated into said variable volume reservoir and a compression reservoir isolated from each other;
   establishing fluid-conducting communication between said pulmonary air passages and said variable volume reservoir; and
   operably associating a mechanical ventilator with said closed-circuit respirator by establishing fluid-conducting communication between said mechanical ventilator and said compression reservoir.

57. The process of claim 56 further comprising the step of effecting positive pressure ventilation of the patient by using said mechanical ventilator to generate pressure waves to actuate said gas impermeable membrane wherein pressure is exerted on said gas flow path.

58. The process of claim 55 further comprising the step of pressurizing said variable volume reservoir to effect positive pressure ventilation of said patient.

59. The process of claim 58 further comprising the step of effecting positive pressure ventilation of the patient by applying pressure to said variable volume reservoir using a mechanical ventilator operably associated with said closed-circuit respirator.

60. A process for closed-circuit total liquid ventilation comprising:
   establishing fluid-conducting communication between pulmonary air passages of a patient and a fluid flow path defined by a closed circuit-liquid respirator, said fluid flow path and said pulmonary air passages substantially filled with a circulating liquid respiratory promoter;
   oxygenating the circulating liquid respiratory promoter by introducing oxygen into the closed-circuit liquid respirator to provide oxygenated liquid respiratory promoter;
   circulating said oxygenated liquid respiratory promoter through the fluid flow path and said pulmonary air passages to provide circulating expiratory fluid comprising carbon dioxide; and
   separating at least a portion of said carbon dioxide from the circulating expiratory fluid by passing the expiratory fluid through a liquid scrubber in fluid-conducting communication with said fluid flow path to provide circulating liquid respiratory promoter.

61. The process of claim 60 further comprising the step of thereafter reintroducing said circulating liquid respiratory promoter to the pulmonary air passages.

62. The process of claim 60 wherein said liquid respiratory promoter is a fluorochemical.

63. The process of claim 62 wherein said fluorochemical liquid respiratory promoter selected from the group consisting of FC-75, FC-77, RM-101, Hostinert 130, APF-145, APF-140, APF-125, perfluorodecalin, perfluorooctyl bromide, perfluorobutyltetrahydrofuran, perfluoropropyltetrahydropyran, dimethyladamantane, trimethyl-bicyclononane, and mixtures thereof.

64. The process of claim 60 further comprising oxygenating said circulating liquid respiratory promoter subsequent to said separating step.

65. An apparatus for closed-circuit total liquid ventilation therapy comprising:
   a closed-circuit liquid respirator operably associated with a liquid ventilator, said liquid respirator comprising a patient-connector capable of establishing fluid-conducting communication with pulmonary air passages of a patient and a ventilating conduit sealingly affixed to said patient-connector, said ventilating conduit defining a fluid flow path;
   a closed-circuit vapor separator defining a vapor flow path comprising a carbon dioxide separator in fluid-conducting communication with said vapor flow path; and
   a gas exchanger in fluid-conducting communication with said vapor flow path and said fluid flow path.

66. The apparatus of claim 65 wherein said closed-circuit liquid respirator comprises a pump in fluid-conducting communication with said gas flow path.

67. The apparatus of claim 65 further comprising a respiratory promoter contained in said fluid flow path.

68. The apparatus of claim 67 wherein said respiratory promoter is a fluorochemical.

69. The apparatus of claim 68 wherein said fluorochemical respiratory promoter is perfluorooctyl bromide.

70. The apparatus of claim 68 wherein said fluorochemical respiratory promoter selected from the group consisting of FC-75, FC-77, RM-101, Hostinert 130, APF-145, APF-140, APF-125, perfluorodecalin, perfluorooctyl bromide, perfluorobutyltetrahydrofuran, perfluoropropyltetrahydropyran, dimethyladamantane, trimethyl-bicyclononane and mixtures thereof.

71. An apparatus for closed-circuit liquid ventilation therapy comprising:
   a closed-circuit liquid respirator operably associated with a liquid ventilator, said liquid respirator comprising a patient-connector capable of establishing fluid-conducting communication with pulmonary air passages of a patient and a ventilating conduit sealingly affixed to said patient-connector, said ventilating conduit defining a fluid flow path; and
   a liquid scrubber in fluid-conducting communication with said fluid flow path.

72. The apparatus of claim 71 wherein said liquid scrubber is modular.

73. The apparatus of claim 71 further comprising a respiratory promoter contained in said fluid flow path.

74. The apparatus of claim 73 wherein said fluorochemical respiratory promoter is perfluorooctyl bromide.

75. The apparatus of claim 73 wherein said respiratory promoter is a fluorochemical.

76. The apparatus of claim 75 wherein said fluorochemical respiratory promoter selected from the group consisting of FC-75, FC-77, RM-101, Hostinert 130, APF-145, APF-140, APF-125, perfluorodecalin, perfluorooctyl bromide, perfluorobutyltetrahydrofuran, perfluoropropyltetrahydropyran, dimethyladamantane, trimethyl-bicyclononane and mixtures thereof.

77. A process for closed-circuit total liquid ventilation comprising:
   establishing fluid-conducting communication between pulmonary air passages of a patient and a fluid flow path defined by a closed circuit-liquid respirator, said fluid flow path and said pulmonary air passages substantially filled with a circulating liquid respiratory promoter;
   oxygenating the circulating liquid respiratory promoter by introducing oxygen into the closed-circuit liquid respirator to provide oxygenated liquid respiratory promoter;
   circulating said oxygenated liquid respiratory promoter through the fluid flow path and said pulmonary air passages to provide expiratory fluid comprising carbon dioxide;

introducing an effective carbon dioxide disassociating amount of oxygen to said expiratory fluid to form an expiratory vapor comprising carbon dioxide;

isolating said expiratory vapor comprising carbon dioxide in a closed-circuit vapor separator in fluid-conducting communication with said fluid flow path, said closed-circuit vapor separator defining a vapor flow path comprising a carbon dioxide separator; and contacting said carbon dioxide separator with said expiratory vapor wherein at least a portion of said carbon dioxide is separated to provide a modified vapor.

78. The process of claim 77 wherein said liquid respiratory promoter is a fluorochemical.

79. The process of claim 78 wherein said fluorochemical liquid respiratory promoter selected from the group consisting of FC-75, FC-77, RM-101, Hostinert 130, APF-145, APF-140, APF-125, perfluorodecalin, perfluorooctyl bromide, perfluorobutyltetrahydrofuran, perfluoropropyltetrahydropyran, dimethyladamantane, trimethyl-bicyclononane, and mixtures thereof.

80. The process of claim 78 wherein said liquid respiratory promoter is perfluorooctyl bromide.

81. The process of claim 77 further comprising the step of reintroducing said modified vapor to said fluid flow path.

* * * * *

UNITED STATES PATENT AND TRADEMARK OFFICE
CERTIFICATE OF CORRECTION

PATENT NO.    : 6,041,777
DATED         : March 28, 2000
INVENTOR(S)   : Nicholas Simon Faithfull, Ernest G. Schutt and Mark A. Walters It is certified that error appears in the above-identified patent and that said Letters Patent is hereby corrected as shown below:

Title Page:
Under Inventors:, after "Ernest G. Schutt" please insert --and Mark A. Walters, San Diego".

Signed and Sealed this

Seventeenth Day of July, 2001

*Attest:*

*Attesting Officer*

NICHOLAS P. GODICI
*Acting Director of the United States Patent and Trademark Office*